(12) United States Patent
Toth et al.

(10) Patent No.: US 6,573,337 B1
(45) Date of Patent: Jun. 3, 2003

(54) OLIGOSACCHARIDE SYNTHESIS

(75) Inventors: Istvan Toth, Northolt Middlesex (GB); Gyula Dekany, Ruislip Middlesex (GB); Barry Kellam, Maidstone Kent (GB)

(73) Assignee: Alchemia Pty LTD, Sherwood (AU)

( * ) Notice: Subject to any disclaimer, the term of this patent is extended or adjusted under 35 U.S.C. 154(b) by 0 days.

(21) Appl. No.: 09/242,816

(22) PCT Filed: Aug. 26, 1997

(86) PCT No.: PCT/AU97/00544
§ 371 (c)(1),
(2), (4) Date: Sep. 2, 1999

(87) PCT Pub. No.: WO98/08799
PCT Pub. Date: Mar. 5, 1998

(30) Foreign Application Priority Data

Aug. 26, 1996 (AU) .............................. PO 1905

(51) Int. Cl.[7] ...................... C08F 212/08; C07C 69/73; C07C 62/04

(52) U.S. Cl. ................................ 525/333.6; 525/333.3; 536/124; 560/183; 562/508; 562/510

(58) Field of Search .......................... 560/183; 562/508, 562/510; 525/333.3, 333.6; 536/124

(56) References Cited
U.S. PATENT DOCUMENTS

| 4,062,950 A | 12/1977 | Frommer et al. | 424/181 |
| 6,335,332 B1 | 1/2002 | Oliva et al. | 514/227.8 |

FOREIGN PATENT DOCUMENTS

| WO | WO 97/45421 | 12/1997 |
| WO | WO 00/42057 | 7/2000 |

OTHER PUBLICATIONS

Caplus abstract of Khim. Geterotsikl. Soedin. vol. 7 pp. 901–904, 1974.*

Ding et al., "Synthesis and Biological Activity of Oligosaccharide Libraries". *Glycoimmunology Plenum Press*, 261–269, 1995.

Garcia Martin et al., "Glycosides of 1–amino–1–deoxy–D–fructose," *Carbohydrate Res.*, 199:139–151, 1990.

Kellam, et al., "Solid phase strategies: applications of 2–acetyl–4–nitroindane–1, 3– dione as a selective protecting group for primary amines," *Tetrahedron*, 54:6817–6832, 1998. abstract only.

Liang, et al., "Parallel synthesis and screening of a solid phase carbohydrate library," *Science*, 274:1520–1522, 1996.

(List continued on next page.)

*Primary Examiner*—James O. Wilson
*Assistant Examiner*—Leigh C. Maier
(74) *Attorney, Agent, or Firm*—Williams, Morgan and Amerson

(57) ABSTRACT

The invention provides a system for solid-phase synthesis of oligosaccharides, based on the discovery that a 2-substituted-1,3-dioxocycloalkyl linker group of general formula (I) can be used to couple saccharide groups of both the O-glycoside and N-glycoside type to a polymer support. The invention provides reagents, reagent kits and methods for solid-phase oligosaccharide synthesis.

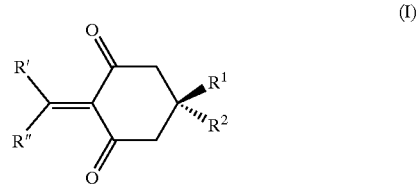

22 Claims, 15 Drawing Sheets

OTHER PUBLICATIONS

Sofia, "Chemical strategies for introducing carbohydrate molecular diversity into the drug discovery process," *Science*, 1–8, 1998.

Protecting Groups in Organic Synthesis, ed. Green & Wuts, John Wiley & Sons, pp. 591–592, 1999.

Bannwarth et al., "A new linker for primary amines applicable to combinatorial approaches," *Biorganic and Med. Chem. Lett.*, 6(13):1525–1528, 1996.

Boons, "Strategies in oligosaccharide synthesis," *Tetrahedron*, 52(4):1095–1121, 1996.

Bycroft et al.. "A Novel Lysine–protecting Procedure for Continuous Flow Solid Phase Synthesis of Branched Peptides," *J. Chem. Soc., Chem. Commun.*, 778–779, 1993.

Chan et al.. "A Novel 4–Aminobenzyl Ester–based Carboxy–protecting Group for Synthesis of Atypical Peptides by Fmoc–Bu$^t$ Solid–phase Chemistry", *J. Chem. Soc. Chem. Commun.*, 2209–2010, 1995.

Nash et al., "Dde–A selective primary amine protecting group: a facile solid phase synthetic approach to polyamine conjugates," *Tetrahedron Letters*, 37(15):2625–2628, 1996.

International Search Report for parent application, PCT/AU97/00544.

International Search Report from Hungarian Patent Office for Patent Application No. P0000819, dated Dec. 20,2000, mailed to client Jan. 31, 2001, received by client Mar. 21, 2001.

Liu et al., "Synthesis of Thermochromic Spiroindolinebenzopyran–6'–Methylenebarbituric Acid," *Chemical Abstracts*, 131(11):843, Abstract No. 145669h, Sep. 13, 1999, taken from *Xibei Daxue Xuebao, Ziran Kexueban*, 28(6):506–508, 1998.

Wipfler et al., "The Reactivity of the C=N–Double Bond System, XV[1] The Reaction of Anilinomethylene–Barbituric Acids with Methylenactive Nitriles"; *Z. Naturforsch*, 33b:1016–1019, 1978, *with Translation*.

Supplemental Partial European Search Report for Patent Application No. EP 98 94 6145.4, dated Jan. 23, 2002.

* cited by examiner

Conditions: (i) Attachment of sugar-linker conjugate to a resin support.
(ii) Selective deprotection of one sugar hydroxyl group.
(iii) Coupling of next sugar residue.
(iv) Repeat of steps (ii) and (iii) as desired.

NB. The Oligosaccharide can potentially be released in either the protected or deprotected form depending on the choice of monomer protection employed during the synthesis.

OLIGOSACCHARIDE SYNTHESIS

FIELD OF THE INVENTION

This invention relates to methods for synthesis of oligosaccharides, and in particular to methods for solid phase or combinatorial synthesis of oligosaccharides. The invention provides a novel linker-resin, linker-saccharide, or resin-linker-saccharide complex, which in one embodiment enables a saccharide residue to be linked to a soluble or insoluble polymeric support for use as a basis for solid-phase synthesis of oligosaccharides. In a second embodiment, the complex of the invention enables oligosaccharides to be linked to a solid polymeric support for use as an analytical reagent.

BACKGROUND OF THE INVENTION

Oligosaccharides constitute a major class of bioactive polymers, implicated in biochemical processes (Lasky, 1992; Varki, 1993) as diverse as cellular differentiation, hormone-cell recognition and cell-cell adhesion, especially viral-host cell (Gambaryan et al, 1995) and bacteria-host cell attachment (Boren et al, 1993). Involvement of oligosaccharides in diseases such as cancer, cardiovascular disorders, microbial infections, graft rejection and autoimmune disorders has therefore, been strongly suggested. Conjugation of carbohydrates to bioactive peptides has also been demonstrated to stabilise the peptides against degradation, and, in more specific circumstances, to facilitate peptide transport across biological barriers (Lee, 1989; Fisher, 1991; Rodriguez, 1989). Thus the ability to synthesise oligosaccharides in a facile and efficient manner is now becoming an extremely important area within organic chemistry.

The highly labour intensive solution phase strategies hitherto utilised in oligosaccharide syntheses require an extremely specialised knowledge and a high degree of chemical skill. This situation was mirrored within the area of peptide synthesis, until Merrifield et al proposed and developed Solid Phase Peptide Synthesis (SPPS) over thirty years ago (Merrifield, 1963). In SPPS immobilisation of the first amino acid of the required sequence to an insoluble resin enabled large excesses of reagents to be used to achieve the coupling of the second amino acid. Any unused materials remaining at the end of the coupling step could then be removed simply by washing the resin beads. This technology meant that the chemist could drive each coupling reaction to almost quantitative yields, and since the peptide intermediates formed were still bound to the resin, purification after each acylation step was not required. SPPS enables peptide and polypeptide synthesis to be employed as a routine research and synthetic tool, and permits large-scale combinatorial synthesis of peptides for screening of potential pharmaceutical agents.

For many years chemists have attempted to transpose this solid-phase methodology to oligosaccharide synthesis, with varying degrees of success. The first attempt was approximately 25 years ago (Frechet and Schuerch, 1971; Frechet and Schuerch, 1972; Guthrie et al, 1971; Guthrie et al, 1973). However, the ozone-mediated deprotection product was an aldehyde-substituted glycoside. Danishefsky and coworkers described the solid phase synthesis of the Lewis b Antigen (Randolph et al, 1995) and N-linked glycopeptides (Roberge et al, 1995) by initial attachment of the primary sugar unit of the oligosaccharide to a 1% divinylbenzene-styrene co-polymer support via a silyl ether linkage. The resin-bound sugar moeity was in this instance a glycal, with on-resin activation achieved via epoxidation of the double bond, and the resulting glycal residue acting as a sugar donor through nucleophile ring-opening of the epoxide. Since there are no calorimetric methods available to the sugar chemist to monitor on-resin glycosylations, the only means of assessing the progress of the reaction is by lysis of the oligosaccharide-resin bond and subsequent analysis of the cleavage product, usually by thin layer chromatography. The tetra-n-butylammonium fluoride-mediated deprotection conditions required to cleave Danishefsky's silyl ether linker are both hazardous and slow. This coupled with the requirement for on-resin activation of the tethered glycals, makes the overall strategy and methodology far from ideal.

In an alternative approach, Douglas and coworkers described the synthesis of D-mannopentose using a poly-ethyleneglycol ω-monomethylether co-polymer and a succinoyl or an α,α'-dioxyxylyl diether linker (Douglas et al, 1995). The reactions were carried out in solution phase, with removal of unused reactants being achieved by precipitation of the oligosaccharide-polymer complex and subsequent washing. In the latter example, cleavage of the oligosaccharide-polymer bond was achieved through catalytic hydrogenation, which required exposure of the conjugate to 1 atm of $H_2$ for 48 h to achieve respectable yields. This again is far too slow to allow effective monitoring of individual glycosylation reactions. Yan et al reported sulphoxide-mediated glycosylation on a Merrifield resin, using a thiophenol linker for the attachment of the primary sugar residue (Yan et al, 1994). This method resulted in the construction of (1–6)-linked oligosaccharides, and was suitable for synthesis of both α- and β-glycosidic linkages. However, the thioglycosidic linkage to the resin dictates that similar sugar donors cannot be employed in this strategy.

Recently Rademann and Schmidt reported the use of trichloroacetimidate sugar donors to a resin bound sugar tethered via an alkyl thiol (Rademann and Schmidt, 1996); once again, however, this method precludes the use of the far superior thioglycoside sugar donors. Meanwhile, Adinolfi et al described the synthesis of disaccharides using a polyethyleneglycol-polystyrene resin, with connection of the first sugar to the polymeric support through a succinate spacer (Adinolfi et al, 1996). However, the acid lability displayed by this linker means that the primary sugar cannot be linked to the resin via the glycosidic position.

The above examples serve to illustrate that the critical element in solid phase synthesis is the nature of the linker between the solid support and the initial synthon. The linker must display excellent stability to the conditions of coupling and deprotection, yet in the case of solid phase oligosaccharide synthesis, it should also be rapidly and efficiently cleaved to allow monitoring of the progress of individual coupling reactions. The cleavage should ideally be achieved by the use of a relatively innocuous chemical reagent.

It is clear, then, that there remains a need in the art for simple, efficient and economical methods for solid-phase synthesis of oligosaccharides.

A hydrazine-labile primary amino-protecting group, N-1-(4,4-dimethyl-2,6-dioxocyclohexylidene)ethyl (Dde), has been reported for protection of lysine side chains during SPPS (Bycroft et al, 1993). This group was modified for use as a carboxy-protecting group in SPPS when the 2-(3-methylbutyryl)dimedone analogue of 2-acetyl-dimedone was condensed with 4-aminobenzylalcohol to afford 4-[N-[1-(4,4-dimethyl-2,6-dioxocyclohexylidene)-3-methylbutyl]-amino] benzyl ester (ODmab)(Chan et al, 1995).

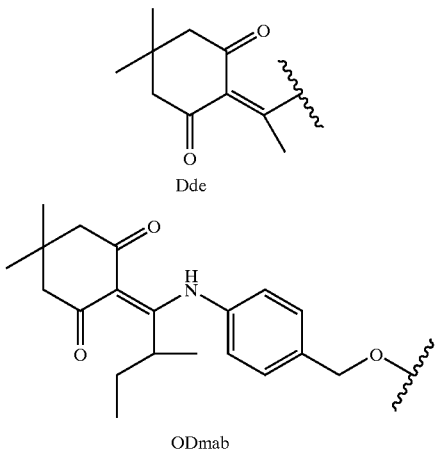

Dde

ODmab

The two protecting groups were reported to be stable to the deprotecting conditions widely used in SPPS, ie. trifluoroacetic acid (TFA) or 20% piperidine in dimethyl formamide (DMF). The ethyl ester, 4-[N-(1-(4,4-dimethyl-2,6-dioxocyclohexylidene)ethyl)amino]benzyl ester (ODab) showed small but significant instability to 20% piperidine-DMF. Both Dde and ODmab are linked to amino groups on amino acids, rather than directly to the solid-phase support. Their use in solid-phase oligosaccharide synthesis has not been suggested.

We have now surprisingly found that protecting groups similar to Dde and ODmab can be coupled to a polymeric support, thereby generating a system for the immobilisation of sugars. To this end we have immobilised N- and O-glycosides to the solid support and synthesised oligosaccharides using various sugar donors. The linkers display excellent stability to most acids and secondary/tertiary bases encountered in modern synthetic chemistry, yet are rapidly and efficiently cleaved with either ammonia, hydrazine or primary amines.

Bannwarth et al have independently developed a different solid phase linker around the Dde protecting group, which they have utilised for the immobilisation of amino acids and primary amines for combinatorial library synthesis (Bannwarth et al, 1996). However, the synthesis of this linker is both protracted and inefficient, and the linker only displays a limited stability to secondary bases such as piperidine. There has been no suggestion that this linker could be used for oligosaccharide synthesis. The linkers we have developed demonstrate a far greater stability than those of Bannwarth et al.

SUMMARY OF THE INVENTION

In one aspect, the invention provides a support for solid-phase synthesis of oligosaccharides, said support comprising:
a) a resin,
b) a linker covalently attached to the resin, and
c) one or more saccharide groups covalently attached to the resin via the linker,
   wherein the linker is a 2-substituted-1,3-dioxocycloalkane compound, and
   said support having general formula I:

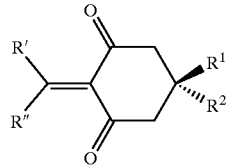

in which
R$^1$ and R$^2$ may be the same or different, and is each hydrogen or C$_{1-4}$ alkyl;
R' is an amino sugar, a glycosylamine, or a glycosylamine of an oligosaccharide; a mono or oligosaccharide coupled through an alkyl-, substituted alkyl-, aryl-, substituted aryl-, cycloalkyl-, or substituted cycloalkyl-amino group; or a mono or oligosaccharide coupled through a carboxyalkyl-, substituted carboxyalkyl-, carboxyaryl-, substituted carboxyaryl-, carboxycycloalkyl-, or substituted carboxycycloalkyl-amino group; and
R'' is an alkyl, substituted alkyl, aryl, substituted aryl, cycloalkyl, or substituted cycloalkyl spacer group which is directly coupled to the resin support, or which may optionally be coupled to the resin support via a suitable covalent linkage, which is stable to conditions of oligosaccharide synthesis and cleavage.

The covalent linkage to the resin may suitably be provided by a —CONH—, —O—, —S—, —COO—, —CH═N—, —NHCONH—, —NHCSNH, or —NHNH— grouping, eg. Spacer-CONH-resin, Spacer-O-resin, Spacer-S-resin, Spacer-CO$_2$-resin, Spacer-CH═N-resin, Spacer-NHCONH-resin, Spacer-NHCSNH-resin, Spacer-NHNH-resin. Other possible covalent linking groups will be known to those skilled in the art.

Preferably both R$^1$ and R$^2$ are methyl.

Preferably R' is an oligosaccharide-O—CH$_2$—(C$_6$H$_4$)—NH, monosaccharide-O—CH$_2$—(C$_6$H$_4$)—NH, amino-oligosaccharide-CO$_2$CH$_2$—(C$_6$H$_4$)NH, or amino-monosaccharide-CO$_2$CH$_2$—(C$_6$H$_4$)—NH group.

In a particularly preferred embodiment the 2-substituted-1,3-dioxocycloalkane linker is functionalised Dde, Ddh or ODmab. In one very particularly preferred embodiment the support comprises a resin, a linker and a monosaccharide, an oligosaccharide, an aminosaccharide or an amino-oligosaccharide.

In a second aspect, the invention provides a support for solid-phase synthesis comprising a resin and a linker group, wherein the linker is a 2-substituted-1,3-dioxocycloalkane of general formula II:

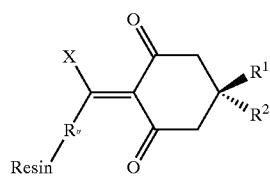

in which
X is OH or NH$_2$;
R$^1$ and R$^2$ may be the same or different, and is each hydrogen or C$_{1-4}$ alkyl; preferably both R$^1$ and R$^2$ are methyl; and R" is an alkyl, substituted alkyl, aryl, substituted aryl, cycloalkyl, or substituted cycloalkyl spacer group which is directly coupled to the resin support, or which may optionally be coupled to the resin support via a suitable covalent linkage, which is stable to conditions of oligosaccharide synthesis and cleavage. The covalent linkage may suitably be provided by a —CONH—, —O—, —S—, —COO—, —CH=N—, —NHCONH—, —NHCSNH, or —NHNH— grouping, eg. Spacer-CONH-resin, Spacer-O-resin, Spacer-S-resin, Spacer-CO$_2$-resin, Spacer-CH=N-resin, Spacer-NHCONH-resin, Spacer-NHCSNH-resin, Spacer-NHNH-resin. Other possible covalent linking groups will be known to those skilled in the art.

In a third aspect, the invention provides a linker-saccharide complex, comprising a linker group of general formula II as defined above and a saccharide group as defined above for R'.

In a fourth aspect the invention provides a linker compound carrying functional groups suitable to attach a primary amine to a resin via covalent bonds which are stable to conditions of oligosaccharide synthesis and cleavage, said compound having general formula III

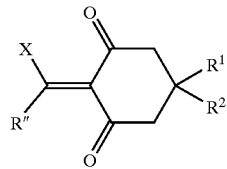

III in which

X is OH or NH$_2$;

R$^1$ and R$^2$ may be the same or different, and is each hydrogen or C$_{1-4}$ alkyl, and R" is an alkyl, substituted alkyl, aryl, substituted aryl, cycloalkyl, or substituted cycloalkyl spacer group, which carries a functionality capable of reacting with a functionalised resin.

Preferably the linker compound is 6-hydroxyl-6-(4,4-dimethyl-2,6-dioxocyclohexylidene)-hexanoic acid or an ester thereof. Preferably the ester is a benzyl, methyl, or t-butyl ester.

For the purposes of this specification the term "substituted" in the definitions of substituents within this specification means that the substituent is itself substituted with a group which does not change the general chemical characteristics of the substituent. Preferred such further substituents are halogen, nitro, amino, hydroxyl, and thiol; preferred halogens are chlorine and iodine. The person skilled in the art will be aware of other suitable substituents of similar size and charge characteristics which could be used as alternatives in a given situation.

For the purposes of this specification a compound is regarded as "stable to conditions of oligosaccharide synthesis and cleavage" if there is less than 10% loss of the compound after exposure at room temperature to ammonia, hydrazine or a primary amino compound in water or DMF. The person skilled in the art will readily be able to determine whether the stability of a particular compound is adequate for it to be useful for the purposes of the invention, using conditions appropriate for his or her particular needs.

The linker compound of the invention may be synthesized on the resin, or may be synthesized in solution.

The invention also provides kits useful in solid phase synthesis or combinatorial synthesis of oligosaccharides, comprising either a) a resin-linker-saccharide support, b) a linker-saccharide complex, or c) a resin-linker support, according to the invention, as described above. The kit may optionally also comprise one or more further reagents such as protecting agents, deprotecting agents, and/or solvents suitable for solid phase or combinatorial synthesis. The person skilled in the art will be aware of suitable further reagents. Different types of kit can then be chosen according to the desired use.

The resin may be any resin which swells in water and/or in an organic solvent, and which comprises one of the following substituents: halogen, hydroxy, carboxyl, SH, NH$_2$, formyl, SO$_2$NH$_2$, or NHNH$_2$, for example methylbenzhydrylamine (MBHA) resin, amino or carboxy tentagel resins, 4-sulphamylbenzyl AM resin. Other suitable resins will be known to those skilled in the art.

The invention also provides a method of solid-phase synthesis of oligosaccharides, comprising the step of sequentially linking mono- or oligosaccharide groups to a support as described above. Similarly the mono- or oligosaccharide building blocks may be as described above.

This method is particularly useful for combinatorial synthetic application.

The linker compound may be synthesised in solution or directly on the resin in a stepwise manner prior to the coupling of the initial sugar group, or the linker-initial sugar conjugate may be synthesised in solution phase and subsequently coupled to the solid support, with subsequent sugars being sequentially attached. Preferably the second and all subsequent sugar groups are coupled to the oligosaccharide chain-resin conjugate after the last sugar in the oligosaccharide chain is partially deprotected.

The invention accordingly provides a method of synthesis of a linker group according to general formula I as defined above, comprising the step of C-acylation of a 2-substituted 1,3-dioxocyclohexane compound with a dicarboxylic acid. Preferably the dicarboxylic acid is mono-protected by ester formation. More preferably the reaction is activated with carbodiimide and catalysed by N,N'-dimethylaminopyridine.

The product of the reaction may optionally be reacted with 4-aminobenzyl alcohol, to form the 4-aminobenzyl derivative.

The invention also provides a method of synthesis of a resin-linker support, comprising the step of swelling a resin in a suitable solvent, treating the swollen resin with a dicarboxylic acid, and reacting the thus-produced product with a 2-substituted 1,3-dioxocycloalkane compound. Preferably for both synthesis of the linker and synthesis of the resin-linker support the 2-substituted 1,3-dioxocyclolkane compound is 5,5-dimethyl-1,3-cyclohexanedione. Also preferably the dicarboxylic acid is adipic acid.

The first sugars attached to the resin-linker unit may be unprotected, partially protected or fully protected glycosides, aminoglycosides, or ether- or amino-linked sugars, where the coupling takes place through a non-glycosidic position.

The building block mono- or oligosaccharide-donors may be any activated sugar, including but not limited to orthoesters, thioorthoesters, cyanoalkylidene derivatives, 1-O-acyl sugars, amino sugars, acetimidates, trichloroacetimidates, thioglycosides, aminoglycosides, amino-oligosaccharides, glycosylamines of oligosaccharides, glycosyl thiocyanates, pentenyl glycosides, pentenoylglycosides, isoprenyl glycosides, glycals, tetramethylphosphoro diamidates, sugar diazirines, selenoglycosides, phosphorodithioates, glycosyldialkylphosphites, glycosylsulphoxides and glycosylfluorides.

Preferably the first sugar coupled to the resin is an aminosugar, an aminoglycoside, or an amino-oligosaccharide or a glycosyl amine of an oligosaccharide.

Preferably partial sugar deprotection is achieved by using acyl-type, trityl, benzyl-type, acetal-type, or various silyl and/or photolabile protecting groups in addition to permanent protecting groups. This permits the synthesis of branched oligosaccharides by using two orthogonal hydroxy-protecting groups on a single sugar donor.

The synthesised oligosaccharide can be cleaved from the resin using ammonia, hydrazine or a primary amine, such as butylamine or cyclohexylamine. For the preparation of aminoglycosides, ammonia or a suitable primary amine in an organic solvent is preferably employed. For the preparation of hydrazides, hydrazine in water or in an organic solvent is preferably employed. For the preparation of oligosaccharides, ammonia in water or in an organic solvent is preferably employed, followed by acidification. When the linker contains a 4-aminobenzyl moiety, after cleavage as described above the first sugar is released still protected by the aminobenzyl group; this can be removed by hydrogenation if desired.

The person skilled in the art will appreciate that the oligosaccharide can be retained on the resin for use as an analytical or preparative reagent, for example in affinity chromatography or for bulk-scale affinity separation.

DETAILED DESCRIPTION OF THE FIGURES

DETAILED DESCRIPTION OF THE INVENTION

Abbreviations used herein are as follows:

| | |
|---|---|
| Bn | Benzyl |
| Bu | Butyl |
| DCM | Dichloromethane |
| Dde | N-1-(4,4-Dimethyl-2,6-dioxocyclohexylidene)ethyl |
| Ddh-OH | 6-Hydroxy-6-(4,4-dimethyl-2,6-dioxocyclohexylidene)hexanoic acid |
| DMAP | N,N'-Dimethyl aminopyridine |
| DMF | N,N'-Dimethylformamide |
| DMTST | Dimethyl(methylthio)sulphonium trifluoromethanesulphonate |
| EEDQ | 1-Isobutyloxycarbonyl-2-isobutyloxy-1,2-dihydroquinoline |
| EtOAc | Ethyl acetate |
| EtOH | Ethanol |
| FAB-MS | Fast atom bombardment mass spectrometry |
| HRMS | High resolution mass spectrometry |
| MBHA | Methyl benzyhydrylamine resin |
| Me | Methyl |
| MeOH | Methanol |
| NMR | Nuclear magnetic resonance |
| ODmab | 4-{N-[1-(4,4-dimethyl-2,6-dioxocyclohexylidene)-3-methylbutyl]-amino}benzyl alcohol. |
| PEG | Polyethylene glycol |
| tBu | tetra-butyl |
| TFA | Trifluoroacetic acid |
| THF | Tetrahydrofuran |
| TLC | Thin-layer chromatography |
| TNBS | 2,4,6-Trinitrobenzene sulphonic acid |

The invention is based upon the immobilisation of a Dde-, Ddh or ODmab-based linker to a polymer support in order to tether any saccharide or oligosaccharide group. This has been illustrated by the coupling of N- and O-glycosides to the linkers, which have been used for oligosaccharide synthesis following coupling to the resin. The nature of these linkers is such that as well as the potential to immobilise any type of sugar, any sugar donor can be subsequently used for oligosaccharide synthesis, thereby allowing rapid and efficient coupling procedures. Suitable sugar donors include, but are not limited to orthoesters, thioorthoesters, cyanoalkylidene derivatives, 1-O-acyl sugars, acetimidates, trichloroacetimidates, thioglycosides, glycosyl thiocyanates, pentenyl glycosides, pentenoylglycosides, isoprenyl glycosides, glycals, tetramethylphosphoro diamidates, sugar diazirines, selenoglycosides, phosphorodithioates, glycosyldialkylphosphites, glycosylsulphoxides and glycosylfluorides.

The stability of the linkers means that orthogonal hydroxy-protecting groups can be employed in sugar protection. These protecting groups include, but are not limited to, acyl-type, trityl, benzyl type, acetal type or various silyl and photolabile protecting groups.

The ease of linker synthesis means that the second functional group on the linker may be a halogen, alcohol, thiol or secondary amine, eg.

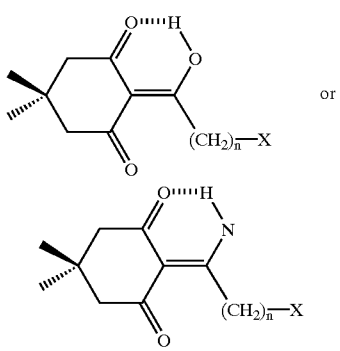

X = Halogen, OH, COOH, SH, NHR

Similarly, the ease of linker synthesis also means that any functionalised resin may be used to immobilise the linker, eg. MBHA resin, amino or carboxy tentagel resins, 4-sulfamylbenzoyl AM resin etc.

Figure 3:
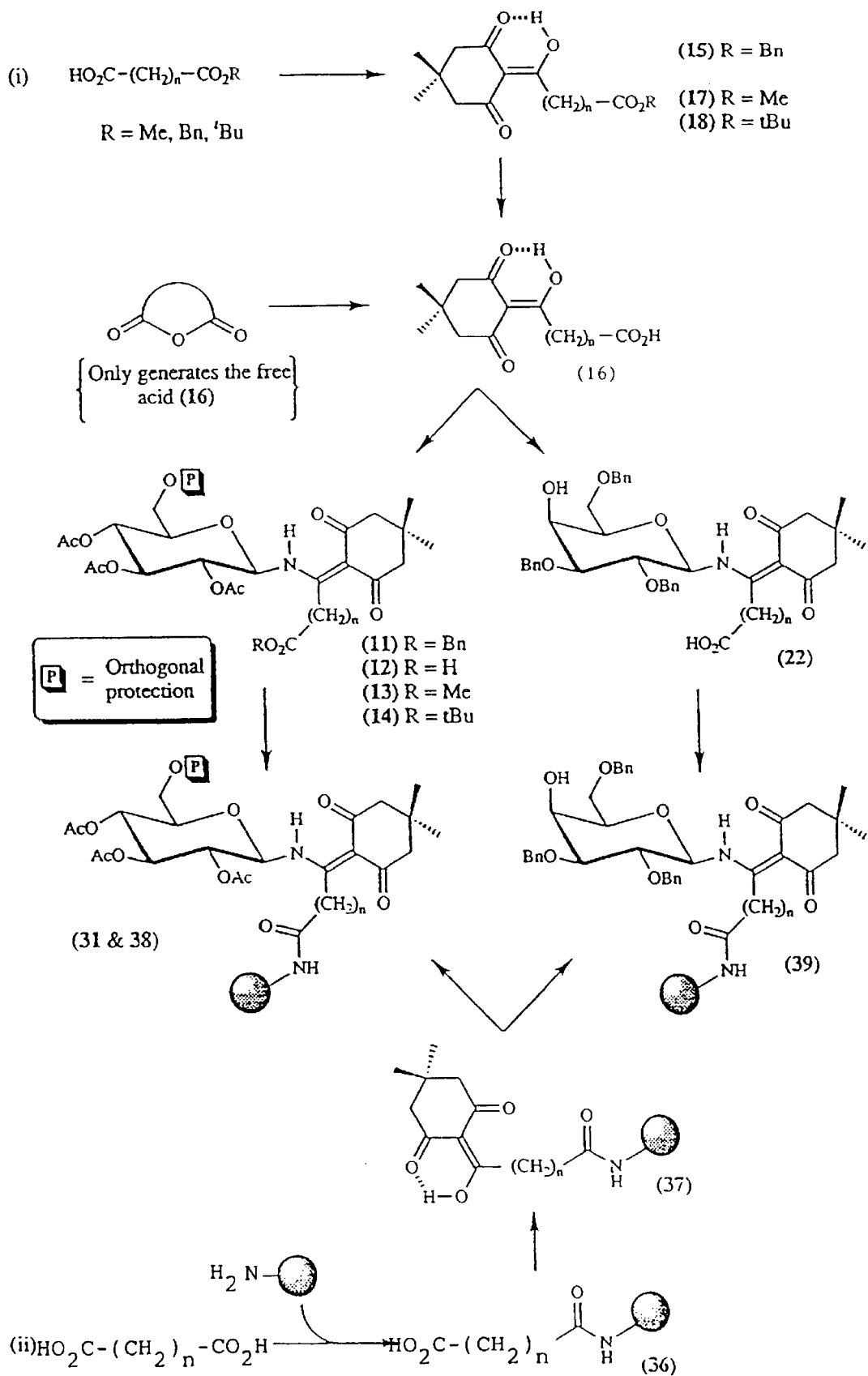
FIG. 3 shows the synthesis of the Dde-based linker of the invention, attachment of the primary sugar residue and coupling of the sugar-linker conjugate to a resin support. An alternative approach whereby the linker is synthesised directly on the resin is also shown.

C-Acylation of dimedone with, for example, a mono-protected di-carboxylic acid is readily achieved via a carbodiimide activated, DMAP catalysed condensation in dry DCM. Removal of the ester protection and coupling of the first amino sugar residue generates a sugar-linker conjugate which can be coupled readily to an amino-functionalised resin support via a carbodiimide-mediated condensation. This reaction can be monitored using conventional amine tests such as TNBS or ninhydrin, to ensure quantitative acylation. Alternatively, the linker can be synthesised directly on the resin, followed by introduction of the first sugar residue on to the linker-resin conjugate. Both methods are illustrated in FIG. 3.

Figure 4:
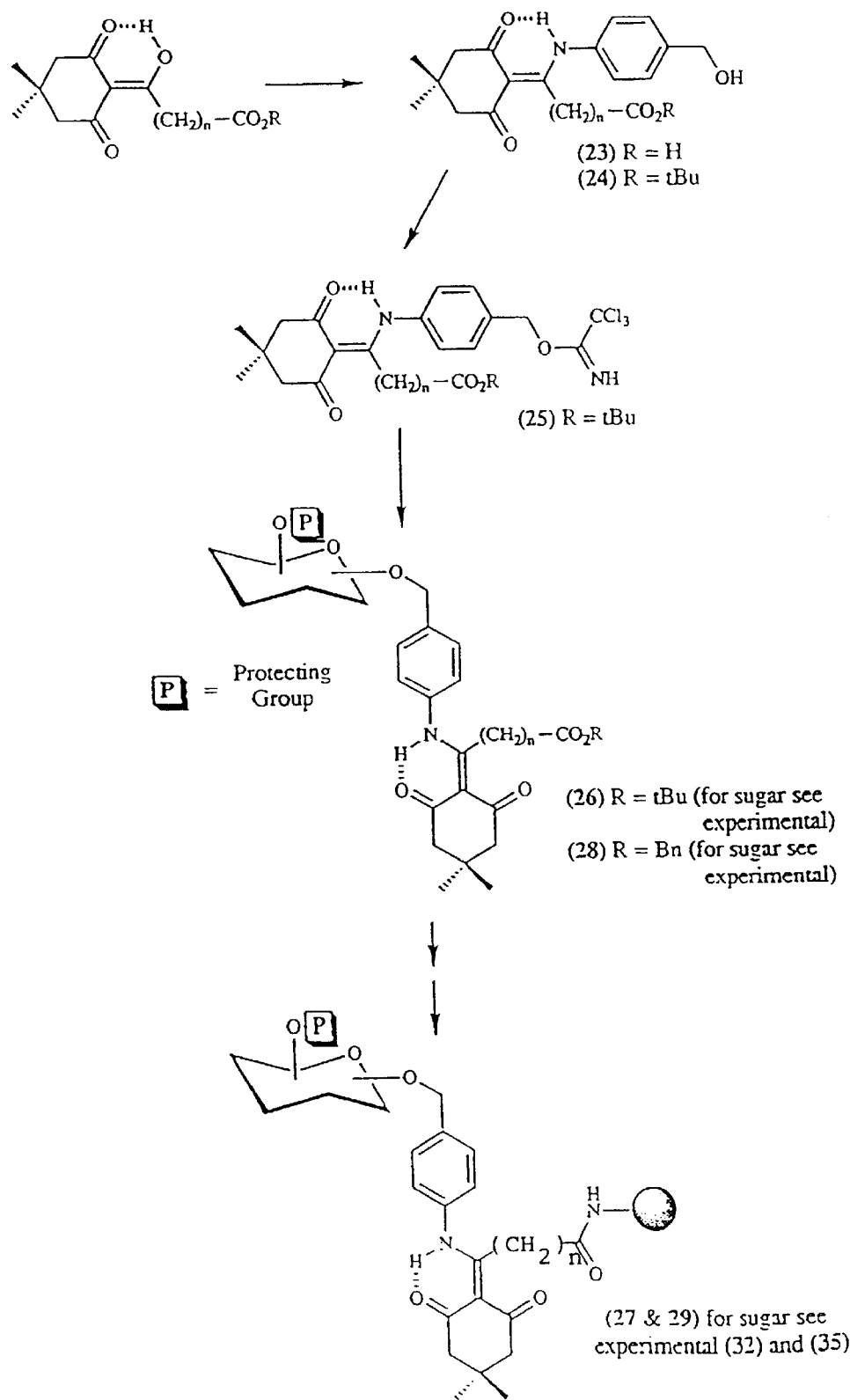
FIG. 4 shows the synthesis of the ODmab-based linker of the invention, attachment of the primary sugar residue and coupling of the sugar-linker conjugate to the resin support.

If an ether-type linkage between the primary sugar residue and the resin is required, then modification of the linker with 4-aminobenzylalcohol to generate the ODmab-type entity allows this method of chemical ligation, as illustated in FIG. 4.

Figure 1:
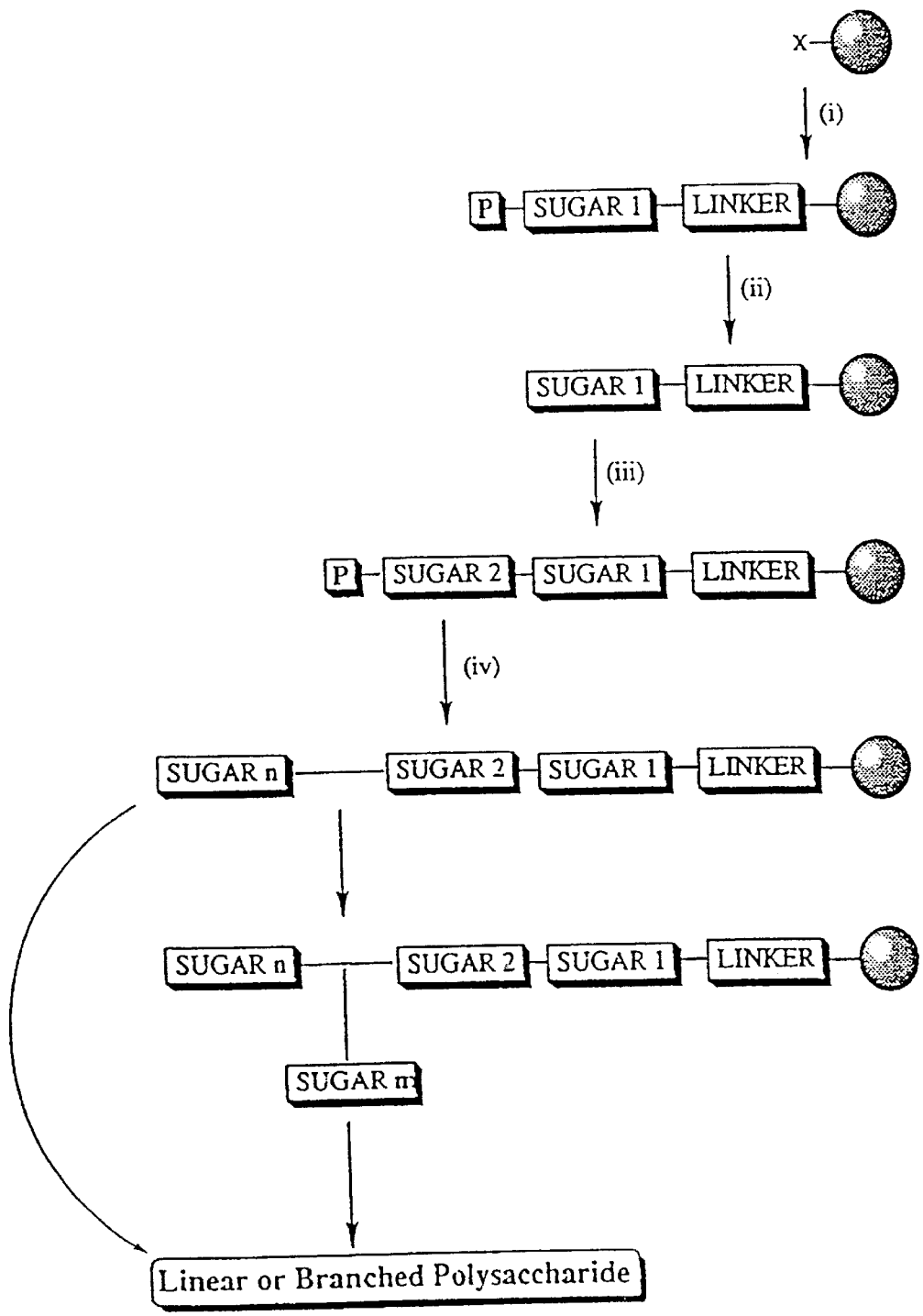
FIG. 1 shows a general representation of the strategy required for solid phase oligosaccharide synthesis.
Figure 5:
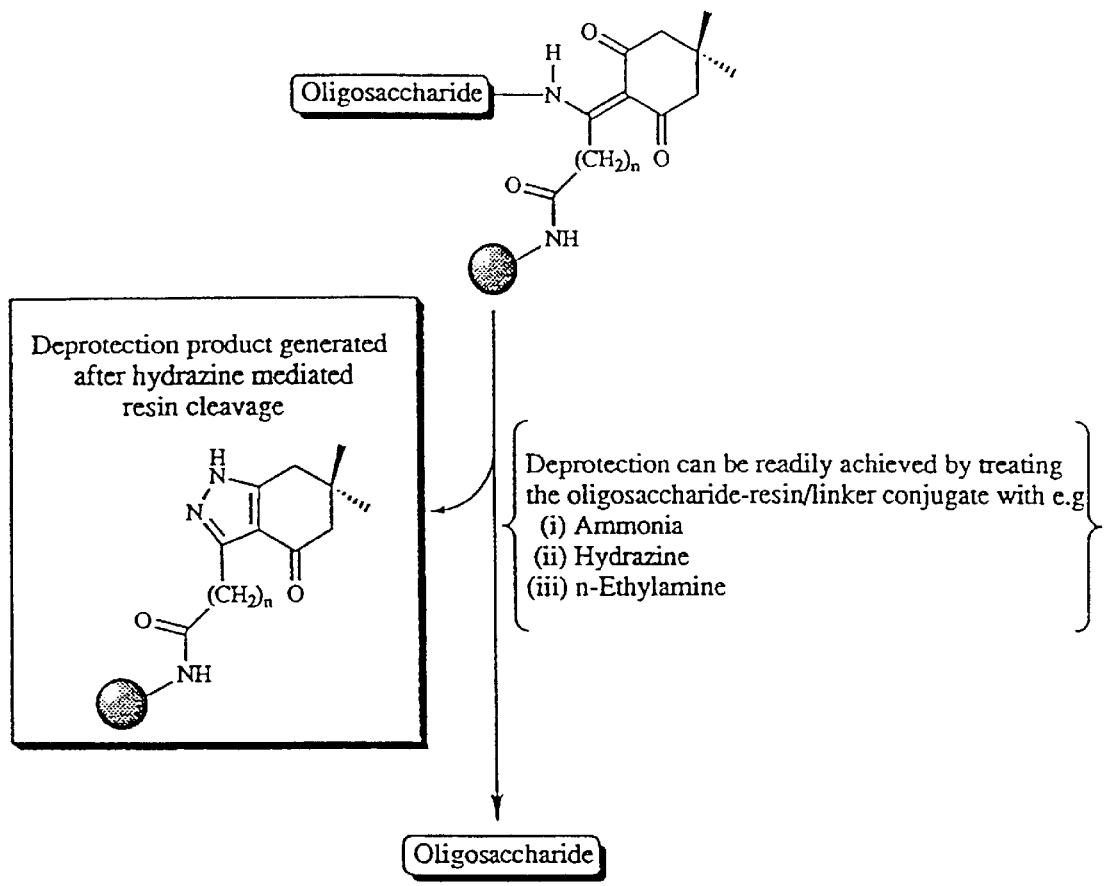
FIG. 5 shows the cleavage of the oligosaccharide-linker bond in a resin-bound hydrazine mediated deprotection product.
Figure 6:
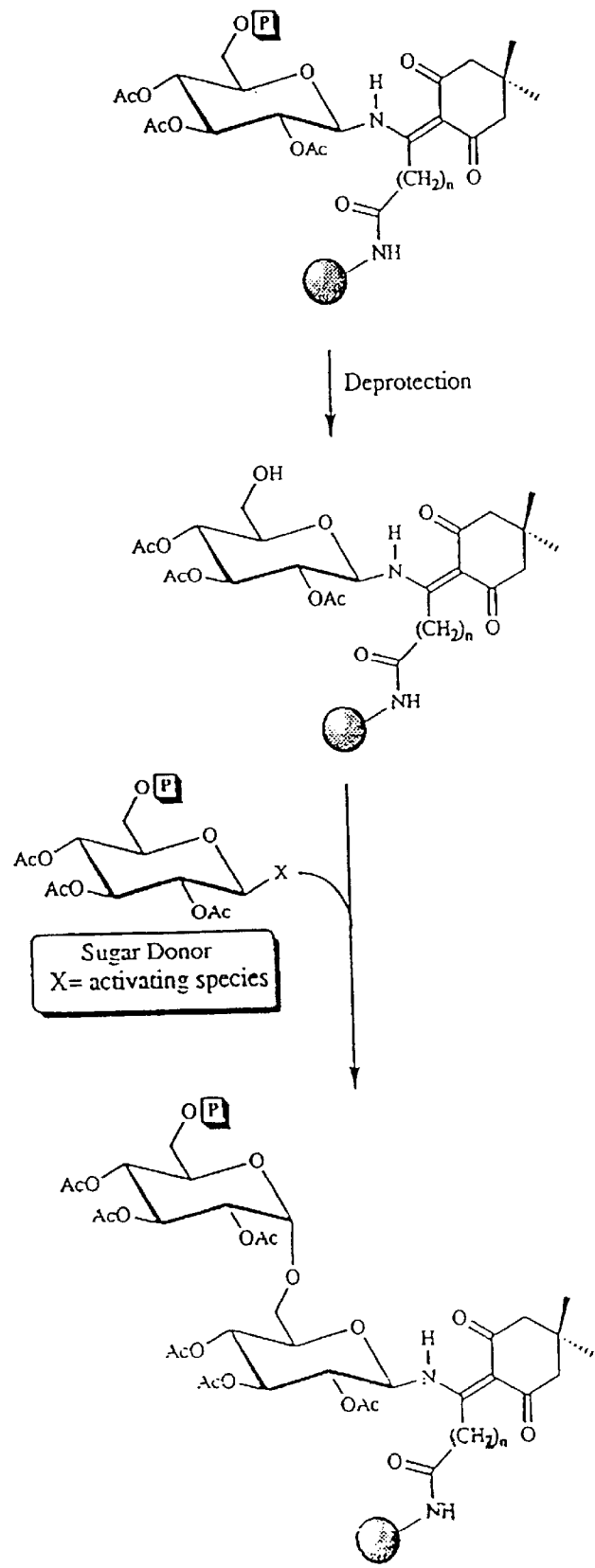
FIG. 6 shows a general representation of the selective deprotection of one sugar hydroxyl group, and subsequent coupling of the next sugar donor.
Figure 8:
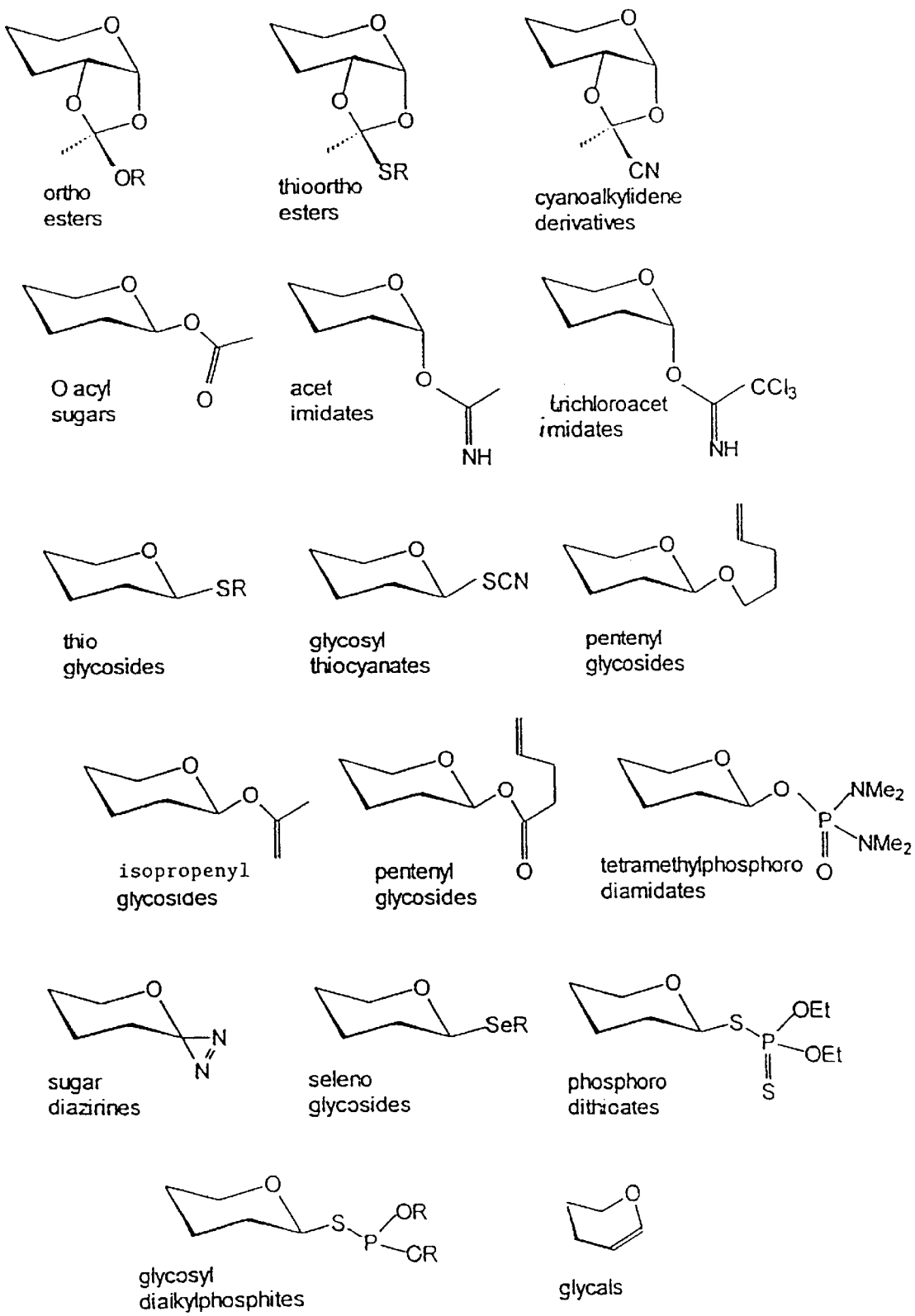
FIG. 8 shows a list of activated sugar donors for solid-phase synthesis.

Following selective deprotection of one hydroxyl group, the second sugar residue is coupled using any of the sugar donors referred to above, as illustrated in FIG. 8. A portion of the resin is readily cleaved using either ammonia, hydrazine or a primary amine, as shown in FIG. 5, and the cleavage mixture is analysed by TLC to monitor the reaction progress. Completion of the reaction is indicated by the disappearance of the monosaccharide. The sequential deprotection and coupling of the following sugar residues is continued until the desired oligosaccharide is complete, as illustrated in FIG. 1. The protecting groups are then removed, and the oligosaccharide is cleaved from the resin support using either ammonia, hydrazine, or a primary amine, in a suitable solvent.

Figure 2:
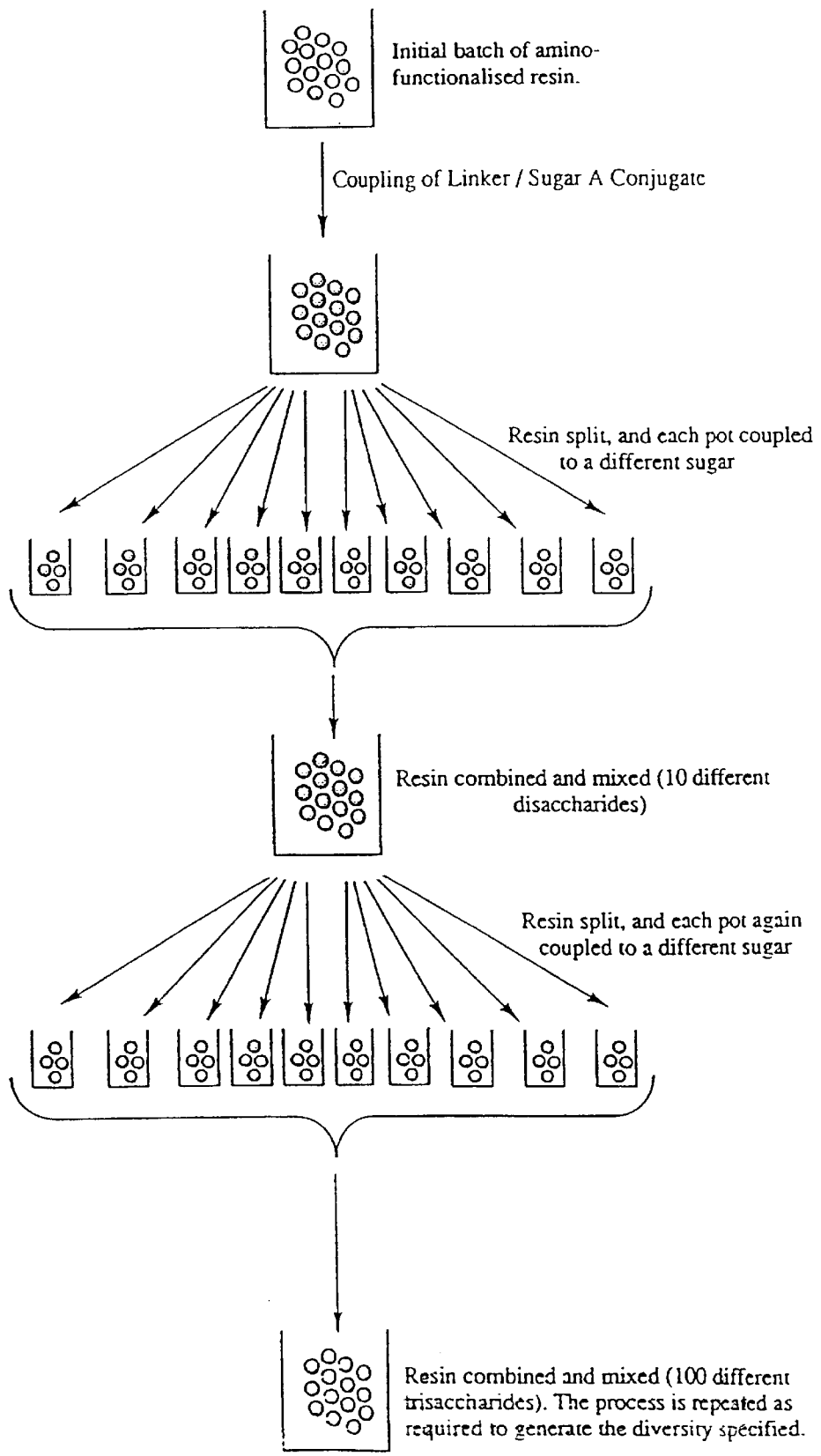
FIG. 2 illustrates a general representation of the 'divide-couple-recombine' method of oligosaccharide library synthesis utilising a solid phase strategy.
Figure 7:
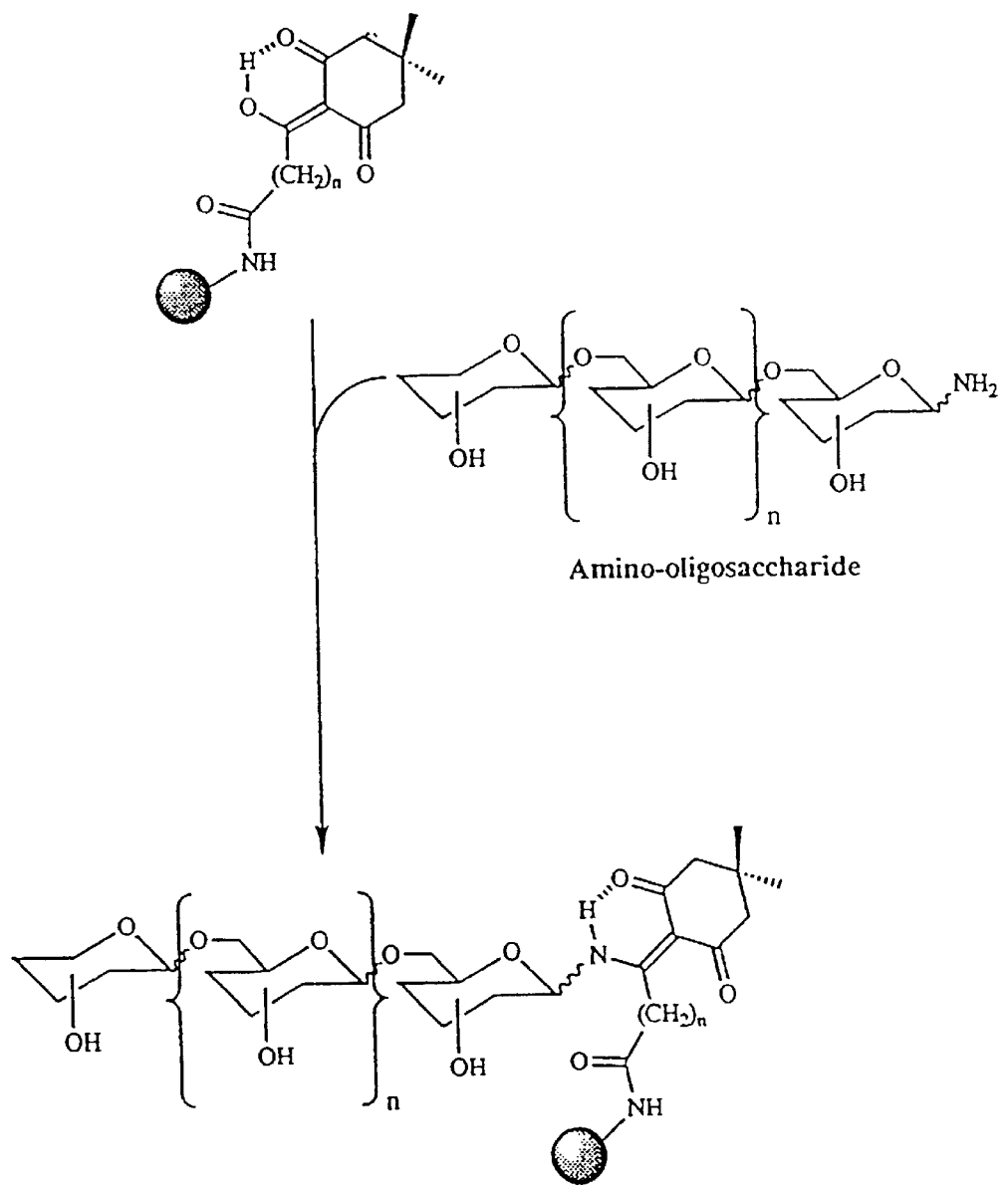
FIG. 7 shows the immobilisation of an amino-oligosaccharide on the Dde-derivatised support.

The resin-linker system of the invention is ideal for the synthesis of combinatorial oligosaccharide libraries, as shown in FIG. 2, and for the immobilisation of mono- or oligosaccharides, as shown in FIG. 7.

The invention will now be described in detail by way of reference only to the following non-limiting examples.

EXAMPLES 1–5

Figure 9:
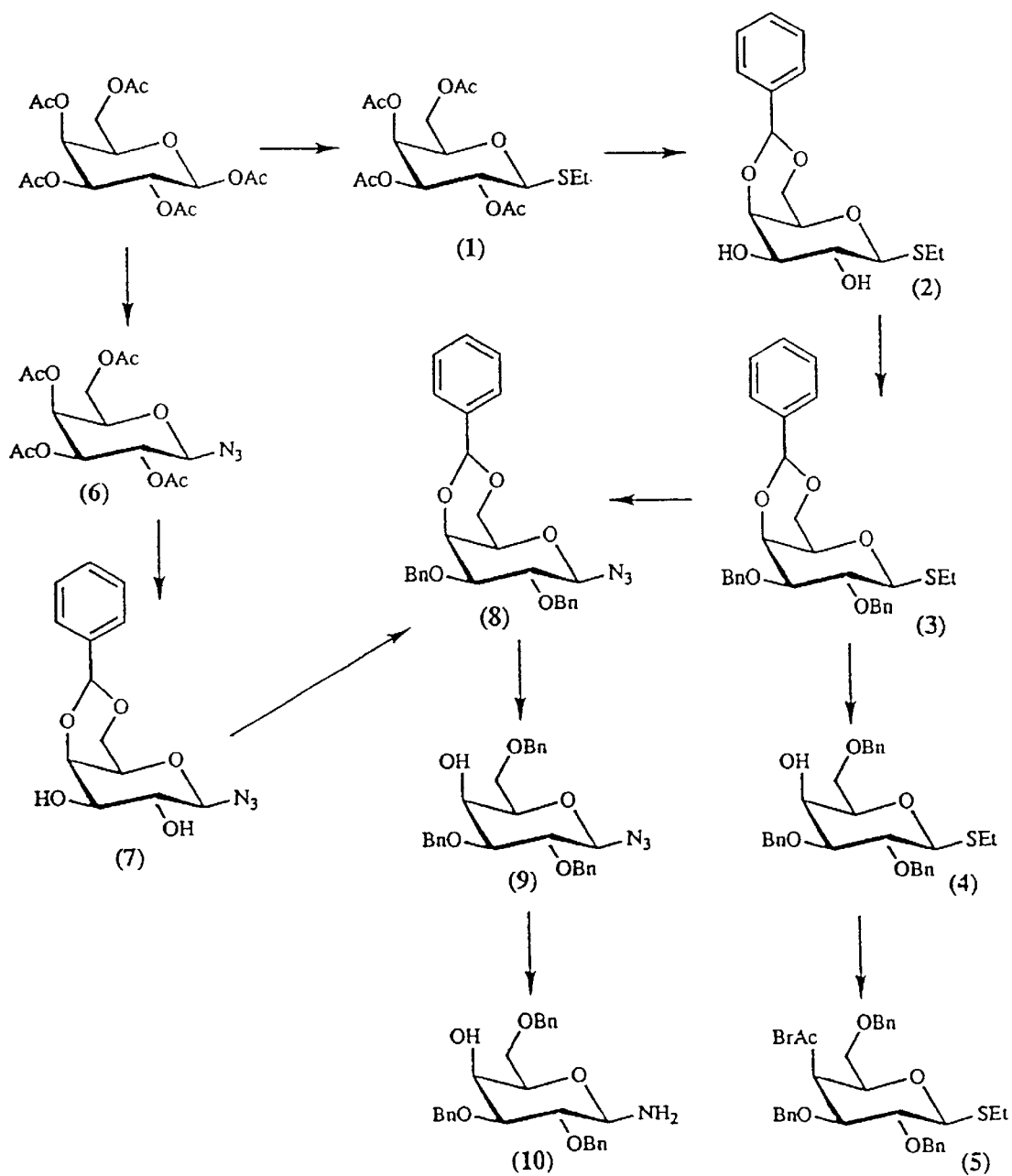
FIG. 9 shows the synthesis of a differentially protected thioglycoside and a partially protected aminoglycoside.

Synthesis of a Specially Protected Thioglycoside-Type Sugar Donor (FIG. 9)

1 Ethyl 2,3,4,6-Tetra-O-acetyl-1-thio-β-D-galactopyranoside

A mixture of galactose pentaacetate (38.00 g, 97.43 mmol), (ethylthio)trimethylsilane (19.60 g, 146.15 mmol) and trimethylsilyl trifluoromethanesulfonate (23.60 g, 106.20 mmol) in $CH_2Cl_2$ (150 ml) was stirred overnight at room temperature. The reaction mixture was diluted with $CH_2Cl_2$ (150 ml) and washed with 1M $Na_2CO_3$ solution (300 ml), water (300 ml), dried over $MgSO_4$ and concentrated. The residue was crystallised from hexane/di-isopropyl ether 1:1 (v/v) to give ethyl 2,3,4,6-tetra-O-acetyl-1-thio-β-D-galactopyranoside (34.00 g, 89%).

$R_f$ 0.43 (hexane/EtOAc 1:1); FAB MS $C_{16}H_{24}O_9S$ (392.3) m/z (%) 415 [M+Na]$^+$ (100), 393 [M+H]$^+$ (20), 331 (56).

2 Ethyl 4,6-O-benzylidene-1-thio-β-D-galacto-pyranoside

A mixture of ethyl 2,3,4,6-tetra-O-acetyl-1-thio-β-D-galactopyranoside (10 g, 25.51 mmol) and sodium methoxide (200 mg, 3.7 mmol) was stirred in abs. MeOH (100 ml) at room temperature for 2 hours. The reaction mixture was neutralised with Amberlite IRA 120 (H+) ion exchange resin and evaporated. The residue was taken up in the (1:?) mixture of benzaldehyde/formic acid (21.2 ml) and stirred at room temperature for 90 minutes. The reaction mixture was diluted with ether (200 ml) and kept at −15° C. for 2 hours. The precipitate formed was collected and purified by chromatography using $CHCl_3$/ethanol 10:3 (v/v) to give ethyl 4,6-O-benzylidene-1-thio-β-D-galacto-pyranoside (8.1 g, 64.5%).

$R_f$ 0.64 ($CHC_3$/ethanol 10:3).

3 Ethyl 2,3-di-O-benzyl-4,6-O-benzylidene-β-D-galactopyranoside

Ethyl 4,6-O-benzylidene-1-thio-β-D-galacto-pyranoside (6.90 g, 22.11 mmol) in 60 ml DMF was added dropwise at 0° C. to a suspension of sodium hydride 60% (2.65 g, 66.34 mmol) in 60 ml DMF. The mixture was stirred at room temperature for 1 hour, then benzyl bromide (11.34 g, 66.34 mmol) was added dropwise at 0° C. The mixture was stirred at room temperature overnight. The mixture was evaporated, and xylene (2×50 ml) was distilled from the residue. The residue was taken up in ether (300 ml) and washed with 2×100 ml water. The organic layer was dried over $MgSO_4$, evaporated and crystallized from MeOH giving ethyl 2,3-di-O-benzyl-4,6-O-benzylidene-1-thio-β-D-galactopyranoside (8.90 g, 82%).

$R_f$ 0.51 hexane/EtOAc 1:1 v/v); $^1$H NMR (CDCl$_3$) δ 7.55–7.25 (m, 15H, 15 Ar—H), 5.47 (s, 1H, CHAr), 4.88–4.75 (4d, 4H, 2 CH$_2$Ar), 4.44 (d, 1H, H-1, $J_{1,2}$=10.89 Hz), 4.30 (dd, 1H, H-6'), 4.16 (d, 1H, H-4), (3.97 (dd, 1H, H-3), 3.88 (t, 1H, H-2), 3.60 (dd, 1H, H-6), 3.35 (d, 1H, H-5), 2.90–2.40 (m, 2H, CH$_2$S), 1.33 (t, 3H, Me); FAB MS $C_{29}H_{32}O_5S$ (492.40) m/z (%) 515 [M+Na]$^+$ (100), 493 [M+H]$^+$ (41), 431 (53).

4 Ethyl 2,3,6-tri-O-benzyl-1-thio-β-D-galacto-pyranoside

A mixture of crude ethyl 2,3-di-O-benzyl-4,6-O-benzylidene-1-thio-β-D-galactopyranoside (5.4 g, 10.97 mmol), sodium cyanoborohydride (6.89 g, 109.7 mmol) and a few grains of methyl orange indicator was stirred in THF (60 ml) at 0° C. THF saturated with HCl was added very slowly until a permanent pink colour was obtained. The reaction mixture was stirred at room temperature for 20 min, then neutralised with dry NH$_3$ and evaporated. The residue was taken up in CHC$_3$ (100 ml), washed with saturated NaHCO$_3$ solution (50 ml), dried over MgSO$_4$ and evaporated. The residue was dissolved in MeOH (50 ml), reflux for 10 min and evaporated. The crude product was purified by chromatography using 1,2-dichloroethane/ethyl acetate 10:0.5 as the mobile phase to give methyl 2,3,6-tri-O-benzyl-1-thio-β-D-galactopyranoside (4.14 g, 75%).

$R_f$ 0.43 (1,2-dichloroethane/EtOAc 10:0.5 v/v); $^1$H NMR (CDCl$_3$) δ 7.40–7.26 (m, 15H, 15 Ar—H), 4.88, 4.76, 4.73, 4.71 (4d, 4H, 2 CH$_2$Ar), 4.57 (s, 2H, CH$_2$Ar), 4.42 (d.1H, H-1, $J_{1,2}$=9.64 Hz), 4.10 (m, 1H, H-4), (3.76 (dd, 1H, H-3), 3.67 (t, 1H, H-2), 3.55 (m, 2H, H-6), 2.75 (m, 2H, CH$_2$S), 2.50 (bs, 1H, OH), 1.31 (t, 3H, CH$_3$); FAB MS C$_{29}$H$_{34}$O$_5$S (494.61) m/z (%) 627 [M+Cs]$^+$ (70), 517 [M+Na]$^+$ (30), 495 [M+H]$^+$ (12).

5 Ethyl 2,3,6-Tri-O-benzyl-4-bromoacetyl-1-thio-β-D-galactopyranoside

A mixture of ethyl 2,3,6-tri-O-benzyl-1-thio-β-D-galactopyranoside (4.14 g, 8.38 mmol), sym. collidine (3.65 g, 30.16 mmol), and 4-dimethylaminopyridine in dry CH$_2$Cl$_2$ (60 ml) was stirred at 0° C. and bromoacetyl bromide (2.53, 2.57 mmol) in CH2Cl$_2$ added dropwise in 15 minutes. The reaction mixture was diluted with CH$_2$Cl$_2$ (100 ml) and washed with 5% HCl solution (3×30 ml) and saturated NaHCO3 solution (30 ml). The solution was dried over MgSO$_4$ and evaporated. The residue was purified by chromatography using hexane/EtOAc 2:1 as the mobile phase to give ethyl 2,3,6-tri-O-benzyl-4-bromoacetyl-1-thio-β-D-galacto-pyranoside (4.84 g, 94%)

$^1$H NMR (CDCl$_3$) δ 7.40–7.25 (m, 15H, 15 Ar—H), 4.80–4.50 (m, 6H, 3 CH$_2$Ar), 4.45 (d, 1H, H-1, $J_{1,2}$=9.53 Hz), 2.73 (m, 2H, CH$_2$S), 1.30 (t, 3H, CH$_3$); FAB MS C$_{31}$H$_{35}$BrO$_6$S (615.56) m/z (%) 638 [M+Na]$^+$ (15), 616 [M+H]$^+$ (32), 509 (80), 463 (21), 419 (18).

EXAMPLES 6–10
Synthesis of a Partially-Protected Glycosyl Amine (FIG. 9)

6 2,3,4,6-Tetra-O-acetyl-β-D-galactopyranosyl Azide 1,2,3,4,6-penta-O-acetyl-galactopyranose (1.17 g, 3 mmol) was dissolved in dry CH$_2$Cl$_2$ (15 ml), then trimethylsilyl azide (416 mg, 3.6 mmol) and SnCl$_4$ (0.18 ml) were added under nitrogen. The mixture was stirred at room temperature for 24 hours. The reaction mixture was subsequently diluted with CH$_2$Cl$_2$ (40 ml), dried over MgSO$_4$ and evaporated. The residue was purified by chromatography using hexane/EtOAc 8:7 v/v as the mobile phase to give 2,3,4,6-tetra-O-acetyl-β-D-galactopyranosyl azide (1.05 g, 94%).

R$_f$ 0.74 (hexane/EtOAc 8:7 v/v); $^1$H NMR (CDCl$_3$) δ 5.41 (d, 1H, H-4), 5.17 (t, 1H, H-2), 5.04 (dd, 1H, H-3), 4.60 (d, 1H, H-1, $J_{1,2}$=10.09 Hz), 4.19 (m, 2H, H-6), 4.00 (m, 1H, H-5), 2.15–1.98 (4s, 12H, 4 OAc); FAB MS C$_{14}$H$_{19}$N$_3$O$_9$ (373.32) m/z (%) 396 [M+Na]$^+$ (100), 374 [M+H]$^+$ (35), 331 (23).

7 4,6-O-benzylidene-β-D-galactopyranosyl Azide

A mixture of 2,3,4,6-tetra-O-acetyl-β-D-galactopyranosyl azide (19.35 g, 51.79 mmol) and sodium methoxide (200 mg, 3.7 mmol) was stirred in abs. MeOH (100 ml) at room temperature for 2 hours. The reaction mixture was neutralised with Amberlite IRA 120 (H+) ion exchange resin and evaporated. The residue was taken up in the mixture of benzaldehyde/formic acid (1:1) (52 ml) and stirred at room temperature for 90 minutes. The reaction mixture was evaporated and the residue was taken up in ether (60 ml) and kept at −15° C. for 2 hours. The precipitate formed was collected by filtration and dried at room temperature affording 4,6-O-benzylidene-β-D-galactopyranosyl azide (11.8 g 78%).

R$_f$ 0.64 (CHC$_3$/ethanol 10:1.5).

8 2,3-di-O-benzyl-4,6-O-benzylidene-β-D-galactopyranosyl Azide 4,6-O-benzylidene-β-D-galactopyranosyl azide (11.8 g, 40.27 mmol) in 60 ml DMF was added dropwise at 0° C. to a suspension of sodium hydride 60% (6.21 g, 155.38 mmol) in 60 ml DMF. The mixture was stirred at room temperature for 1 hour, then benzyl bromide (26.57 g, 155.38 mmol) was added dropwise at 0° C. The mixture was stirred at room temperature overnight. The mixture was evaporated, and xylene (2×50 ml) was distilled from the residue. The residue was taken up in ether (500 ml) and washed with 2×100 ml water. The organic layer was dried over MgSO$_4$ and evaporated, giving methyl 2,3-di-O-benzyl-4,6-O-benzylidene-β-D-galactopyranosyl azide as a crude residue (19.4 g).

9 2,3,6-tri-O-benzyl-β-D-galactopyranosyl Azide

A mixture of crude 2,3-di-O-benzyl-4,6-O-benzylidene-β-D-galactopyranosyl azide (9.00 g, 19.02 mmol), sodium cyanoborohydride (12.00 g, 190.2 mmol) and a few grains of methyl orange indicator was stirred in THF (80 ml) at 0° C. THF saturated with HCl was added very slowly until a permanent pink colour was obtained. The reaction mixture was stirred at room temperature for 20 min, then neutralised with dry NH$_3$ and evaporated. The residue was taken up in CHC$_3$ (100 ml), washed with saturated NaHCO$_3$ solution (50 ml), dried over MgSO$_4$ and evaporated. The residue was dissolved in MeOH (50 ml) and kept under reflux for 10 min and evaporated. The crude product was purified by chromatography using 1,2-dichloro-ethane/EtOAc 10:0.4 as the mobile phase to give 2,3,6-tri-O-benzyl-β-D-galactopyranosyl azide (6.50 g, 72%).

R$_f$ 0.42 (1,2-dichloroethane/EtOAc 10:0.4 v/v); $^1$H NMR (CDCl$_3$) δ 7.40 (m, 15H, 15 Ar—H), 4.90–4.55 (m, 6H, 3 CH$_2$Ar), 4.06 (m, 1H, H-4), (3.82–3.70 (m, 3H, H-3, H-2, H-5), 3.65 (dd, 1H, H-6'), 3.60 (d, 1H, H-1, $J_{1,2}$=8.64 Hz), 3.51 (dd, 1-H, H-6); FAB MS C$_{27}$H$_{29}$N$_3$O$_5$ (475.40) m/z (%) 608 [M+Cs]$^+$ (10), 498 [M+Na]$^+$ (65), 476 [M+H]$^+$ (25), 433 (75), 341 (20).

10 2,3,6-tri-O-benzyl-β-D-galactopyranosyl Amine

A mixture of 2,3,6-tri-O-benzyl-β-D-galactopyranosyl azide (3.00 g, 6.31 mmol), propane-1,3-dithiol (3.40 g, 31.50 mmol), and triethylamine (3.50 g, 31.5 mmol) in MeOH (31 ml) was stirred under nitrogen at room temperature for 10 hours. The reaction mixture was evaporated and purified by chromatography using CHC$_3$/EtOH 10:0.3 v/v to give 2,3,6-tri-O-benzyl-β-D-galactopyranosyl amine (2.66 g, 94%);

R$_f$ 0.38 (CHC$_3$/EtOH 10:0.3 v/v); FAB MS C$_{27}$H$_{31}$NO$_5$ (449.33) m/z (%) 472 [M+Na]$^+$ (75), 450 [M+H]$^+$ (100).

EXAMPLE 11
Synthesis of a Glycosyl Amine-Ddh-Benzyl Ester Conjugate in Solution (FIG. 3)

11 N-(Benzyl 6-(4,4-Dimethyl-2,6-dioxocyclo-hexylidene)-hexanoate-6-yl) 2,3,4,6-Tetra-O-acetyl-β-D-glucopyranosyl Amine A mixture of benzyl 6-hydroxy-6-(4,4-dimethyl-2,6-dioxocyclohexylidene)-hexanoate (932 mg, 2.60 mmol), 2,3,4,6-tetra-O-acetyl-β-D-glucopyranosyl amine in CH$_2$Cl$_2$ (2.0 ml) was stirred at room temperature for 2 days. The reaction mixture was evaporated and purified by chromatography using hexane/EtOAc 1:1 as the mobile phase to give N-(Benzyl 6-(4,4-dimethyl-2,6-dioxocyclohexylidene)-hexanoate-6-yl) 2,3,4,6-tetra-O-acetyl-β-D-glucopyranosyl amine (1.70 g, 95%);

R$_f$ 0.32 (hexane/EtOAc 1:1 v/v); $^1$H NMR (CDCl$_3$) δ 7.37–7.26 (m, 5H, 5 Ar—H), 5.40–5.00 (m, 7H, 7 sugar protons), 3.10, 2.85 (2t, 4H, 2 CH$_2$), 2.38 (2s, 4H, Dde 2 CH$_2$), 2.06–1.98 (4s, 12H, 4 OAc), 1.80 (m, 4H, 2 CH$_2$), 1.02, 1.00 (2s, 6H, Dde 2CH$_3$); FAB MS C$_{35}$H$_{45}$NO$_{13}$ (687.23) m/z (%) 710 [M+Na]$^+$ (35), 688 [M+H]$^+$ (100), 356 (60).

EXAMPLE 12
Synthesis of a Fully Protected Glycosyl Amine-Ddh Conjugate Deprotecting a "Fully Protected Amine—DdH Ester Conjugate" in Solution (FIG. 3)

12 N-(6-(4,4-Dimethyl-2,6-dioxocyclohexylidene)-hexanoic Acid-6-yl) 2,3,4,6-Tetra-O-acetyl-β-D-glucopyranosyl Amine N-(Benzyl 6-(4,4-dimethyl-2,6-dioxocyclo-hexylidene)-hexanoate-6-yl) 2,3,4,6-tetra-O-acetyl-β-D-glucopyranosyl amine (1.27 g, 1.84 mmol) was hydrogenated over Pd/C (10%) (200 mg) in MeOH (20 ml) at room temperature for 10 hours. The catalyst was filtered off, and the filtrate was evaporated and then chromatographed using $CHCl_3/MeOH$ 10:0.5 v/v as the mobile phase to give N-(6-(4,4-dimethyl-2,6-dioxocyclohexylidene)-hexanoic acid-6-yl) 2,3,4,6-tetra-O-acetyl-β-D-glucopyranosyl amine 1.10 g, 98%);

$R_f$ 0.38 ($CHCl_3/MeOH$ 10:0.5 v/v); $^1H$ NMR ($CDCl_3$) δ 5.40–5.00 (m, 7H, 7 sugar protons), 3.15, 2.86 (2t, 4H, 2 $CH_2$), 2.45 (2s, 4H, Dde 2 $CH_2$), 2.10–1.98 (4s, 12H, 4 OAc), 1.80–1.65 (m, 4H, 2 $CH_2$), 1.02, 1.00 (2s, 6H, Dde $2CH_3$); FAB MS $C_{28}H_{39}NO_{13}$ (597.33) m/z (%) 620 [M+Na]+ (55), 598 [M+H]+ (100).

EXAMPLE 13
Synthesis of a Glycosyl Amine-Ddh-Methyl Ester Conjugate in Solution (FIG. 3)
13 N-(Methyl 6-(4,4-Dimethyl-2,6-dioxocyclo-hexylidene)-hexanoate-6-yl) 2,3,4,6-tetra-O-acetyl-β-D-glucopyranosyl amine Reaction 11 was repeated with the difference that methyl 6-hydroxy-6-(4,4-dimethyl-2,6-dioxocyclohexylidene)-hexanoate was used instead of benzyl 6-hydroxy-6-(4,4-dimethyl-2,6-dioxocyclohexylidene)-hexanoate. Yield: 92%;

$R_f$ 0.28 (hexane/EtOAc 1:1 v/v); FAB MS $C_{29}H_{41}NO_{13}$ (611.45) m/z (%) 624 [M+Na]+ (100), 612 [M+H]+ (34).

EXAMPLE 14
Synthesis of a Glycosyl Amine-Ddh-t-Butyl Ester Conjugate in Solution (FIG. 3)
14 N-(t-Butyl 6-(4,4-Dimethyl-2,6-dioxocyclo-hexylidene)-hexanoate-6-yl) 2,3,4,6-Tetra-O-acetyl-β-D-glucopyranosyl Amine Reaction 11 was repeated with the difference that t-butyl 6-hydroxy-6-(4,4-dimethyl-2,6-dioxocyclo-hexylidene)-hexanoate was used instead of benzyl 6-hydroxy-6-(4,4-dimethyl-2,6-dioxocyclohexylidene)-hexanoate. Yield: 96%;

$R_f$ 0.35 (hexane/EtOAc 1:1 v/v); FAB MS $C_{32}H_{47}NO_{13}$ (653.37) m/z (%) 676 [M+Na]+ (80), 677 [M+H]+ (100).

EXAMPLE 15
Synthesis of Ddh-OH Benzyl Ester in Solution (FIG. 3)
15 Benzyl 6-hydroxy-6-(4,4-Dimethyl-2,6-dioxo-cyclohexylidene)-hexanoate To a stirred solution of mono-benzyl adipate (2.36g, 10 mmol) in dry $CH_2Cl_2$ (50 ml) was added 5,5-dimethyl-1,3-cyclohexanedione (1.4 g, 10 mmol), N,N'-dicyclohexylcarbodiimide (2.1 g, 10.1 mmol) and 4-dimethylaminopyridine (1.22 g, 10 mmol). The resulting solution was allowed to stir at room temperature for 18 h. The solution was cooled and filtered to remove the precipitated N,N'-dicyclohexylurea. The filtrate was evaporated and the residue redissolved in EtOAc (50 ml) and washed with 1 M $KHSO_4$. The organic extract was washed with brine (92×10 ml), dried ($MgSO_4$) and evaporated to yield a white/yellow amorphous powder. Flash silica chromatography (EtOAc/hexane 1:2 v/v) afforded benzyl 6-hydroxy-6-(4,4-dimethyl-2,6-dioxocyclohexylidene)-hexanoate (3.00 g, 84%) as a white crystalline solid. $^1H$ NMR ($CDCl_3$) δ 18.10 (s, 1H, OH), 7.30 (s, 5H, 5Ar—H), 5.06 (s, 2H, $CH_2Ar$), 3.00 (t, 2H, $CH_2$), 2.47 (s, 2H, Dde $CH_2$), 2.35 (t, 2H, $CH_2CO_2$), 2.29 (s, 2H, Dde $CH_2$), 1.65 (m, 4H, 2 $CH_2$), 1.01 (s, 6H, 2 CH3); FAB MS $C_{21}H_{26}O_5$ (358.18) m/z (%) 359 [M+H]+ (100), 267 (40); HRMS (FAB) Found: m/z 359.1858 Calcd for $C_{21}H_{27}O_5$: (M+H), 359.1850.

EXAMPLE 16
Synthesis of Ddh-OH by Deprotection of a Ddh-OH Ester (FIG. 3)
16 6-hydroxy-6-(4,4-Dimethyl-2,6-dioxocyclo-hexylidene)-hexanoic Acid Benzyl 6-hydroxy-6-(4,4-dimethyl-2,6-dioxocyclo-hexylidene)-hexanoate (1.50 g, 4.19 mmol) was hydrogenated over Pd/C (10%) (150 mg) in MeOH (20 ml) at room temperature for 10 hours. The catalyst was filtered off, and the filtrate was evaporated, yielding 6-hydroxy-6-(4,4-dimethyl-2,6-dioxocyclohexylidene)-hexanoic acid (1.10 g, 98%);

$R_f$ 0.35 (hexane/EtOAc 2:1 v/v); FAB MS $C_{14}H_{20}O_5$ (268.12) m/z (%) 313 [M+2Na]+ (34), 291 [M+Na]+ (100), 269 [M+H]+ (16).

EXAMPLE 17
Synthesis of a Ddh-OH Methyl Ester in Solution (FIG. 3)
17 Methyl 6-hydroxy-6-(4,4-Dimethyl-2,6-dioxo-cyclohexylidene)-hexanoate Reaction 15 was repeated, with the difference that mono-methyl adipate was used instead of mono-benzyl adipate, and afforded methyl 6-hydroxy-6-(4,4-dimethyl-2,6-dioxocyclohexylidene)-hexanoate (2.39 g, 85%).

$R_f$ 0.32 (EtOAc/hexane 1:2 v/v) FAB MS $C_{15}H_{22}O_5$ (282.22) m/z (%) 305 [M+H+ (100), 283 [M+H]+ (66).

EXAMPLE 18
Synthesis of Ddh-OH t-Butyl Ester in Solution (FIG. 3)
18 t-Butyl 6-hydroxy-6-(4,4-Dimethyl-2,6-dioxocyclo-hexylidene)-hexanoate Reaction 15 was repeated, with the difference that mono-t-butyl adipate was used instead of mono-benzyl adipate, and afforded t-butyl 6-hydroxy-6-(4,4-dimethyl-2,6-dioxocyclohexylidene)-hexanoate (2.62 g, 81%).

$R_f$ 0.36 (EtOAc/hexane 1:2 v/v) FAB MS $C_{18}BH_{28}O_5$ (324.41) m/z (%) 347 [M+H]+ (100), 325 [M+H+ (43), 267 (80).

EXAMPLE 19
Synthesis of Ddh-OH by Deprotection of a Ddh-OH t-Butyl Ester (see 16, FIG. 3)
19 6-hydroxy-6-(4,4-Dimethyl-2,6-dioxocyclo-hexylidene)-hexanoic Acid t-Butyl 6-hydroxy-6-(4,4-dimethyl-2,6-dioxocyclo-hexylidene)-hexanoate (100 mg, 0.30 mmol) was dissolved in $CH_2Cl_2$/TFA 1:1 mixture (2 ml) and stirred at room temperature for 1 h. The reaction mixture was evaporated giving 6-hydroxy-6-(4,4-dimethyl-2,6-dioxocyclohexylidene)-hexanoic acid (0.81 g, 98%)

EXAMPLE 20
Synthesis of Ddh-OH from Cyclic Anhydrides (see 16, FIG. 3)
20 6-hydroxy-6-(4,4-Dimethyl-2,6-dioxocyclo-hexylidene)-hexanoic Acid A mixture of glutaric anhydride (2.28 g, 20 mmol), dimedone (2.8 g, 20 mmol), 4-dimethylamino-pyridine (3.99 g, 30 mmol) in abs. pyridine (50 ml) was stirred at room temperature for 24 h. The reaction mixture was evaporated and the residue was taken up in $CHCl_3$ (100 ml), washed 5% HCl solution (3×25 ml), saturated $NaHCO_3$ solution, dried over $MgSO_4$ and evaporated. The residue was purified by chromatography using ether/acetic acid (10 ml:1 drop) as the mobile phase to give 6-hydroxy-6-(4,4-dimethyl-2,6-dioxocyclohexylidene)-hexanoic acid (2.28 g, 45%).

EXAMPLE 21
Synthesis of a Fully Protected Glycosyl Amine-Ddh Conjugate Using Ddh-OH in Solution (See 12, FIG. 3)
21 N-(6-(4,4-Dimethyl-2,6-dioxocyclohexylidene)-hexanoic Acid-6-yl) 2,3,4,6-Tetra-O-acetyl-β-D-glucopyranosyl Amine A mixture of 6-hydroxy-6-(4,4-dimethyl-2,6-dioxocyclohexylidene)-hexanoic acid (400 mg, 1.49 mmol), 2,3,4,6-tetra-O-acetyl-β-D-glucopyranosyl amine (259 mg, 0.74 mmol) in abs. EtOH was stirred under reflux for 2 h. The reaction mixture was evaporated and chromatographed using CHCl3/MeOH 10:0.5 v/v to give N-(6-(4,4-dimethyl-2,6-dioxocyclohexylidene)-hexanoic acid-6-yl) 2,3,4,6-tetra-O-acetyl-β-D-glucopyranosyl amine(410 mg, 92%).

EXAMPLE 22
Synthesis of a Partially Protected Glycosyl Amine-Ddh Conjugate Using Ddh-OH in Solution (FIG. 3)
22 N-(6-(4,4-Dimethyl-2,6-dioxocyclohexylidene)-hexanoic Acid-6-yl) 2,3,6-tri-0-benzyl-β-D-galactopyranosyl Amine Reaction 21 was repeated with the difference that 2,3,6-tri-O-benzyl-β-D-galactopyranosyl amine was used instead of 2,3,4,6-tetra-O-acetyl-β-D-glucopyranosyl amine, and afforded N-(6-(4,4-dimethyl-2,6-dioxocyclo-hexylidene)-hexanoic acid-6-yl) 2,3,6-tri-O-benzyl-β-D-galactopyranosyl amine (299 mg, 90%).

$R_f$ 0.34 (CHCl$_3$/MeOH 10:0.1 v/v) FAB MS C$_{37}$H$_{43}$NO$_7$ (613.41) m/z (%) 649 [M+2Na]$^+$ (34), 626 [M+Na]$^+$ (100), 614 [M+H]$^+$ (65).

EXAMPLE 23
Synthesis of Ddh-Aminobenzyl Linker in Solution (FIG. 4)
23 N-(6-(4,4-Dimethyl -2,6-dioxocyclohexylidene)-hexanoic Acid-6-yl) 4-amino-benzylalcohol Reaction 21 was repeated with the difference that 4-aminobenzyl alcohol was used instead of 2,3,4,6-tetra-O-acetyl-β-D-glucopyranosyl amine, and afforded N-(6-(4,4-dimethyl-2,6-dioxocyclohexylidene)-hexanoic acid-6-yl) 4-aminobenzyl alcohol (259 mg, 94%).

$R_f$ 0.40 (EtOAc/hexane/acetic acid 2:1:0.1 v/v/v); FAB MS C$_{21}$H$_{27}$NO$_5$ (373.43) m/z (%) 418 [M+2Na]$^+$ (24), 396 [M+Na]$^+$ (100), 374 [M+H]$^+$ (35).

EXAMPLE 24
Synthesis of Ddh-Aminobenzyl t-Butyl Ester Linker in Solution (FIG. 4)
24 N-(t-Butyl 6-(4,4-Dimethyl-2,6-dioxocyclo-hexylidene)-hexanoate-6-yl) 4-aminobenzyl Alcohol A mixture of t-butyl 6-hydroxy-6-(4,4-dimethyl-2,6-dioxocyclohexylidene)-hexanoate (400 mg, 1.23 mmol) and 4-aminobenzyl alcohol (605 mg, 4.92 mmol) in abs. EtOH was stirred under reflux for 2 h. The reaction mixture was evaporated and purified by chromatography using CHCl$_3$/MeOH 9:1 as the mobile phase to give N-(t-Butyl 6-(4,4-dimethyl-2,6-dioxocyclohexylidene)-hexanoate-6-yl) 4-aminobenzyl alcohol (395 mg, 75%)

$R_f$ 0.52 (CHC$_3$/MeOH 9:1 v/v) FAB MS C$_{25}$H$_{35}$NO$_5$ (429.53) m/z (%) 452 [M+Na]$^+$ (100), 430 [M+H]$^+$ (32), 372 (64).

EXAMPLE 25
Synthesis of Ddh-Aminobenzyl t-Butyl Ester Trichloroacetimidate Activated Linker in Solution (FIG. 4)
25 N-(t-Butyl 6-(4,4-Dimethyl-2,6-dioxocyclo-hexylidene)-hexanoate-6-yl) 4-Aminobenzyl Trichloroacetimidate A mixture of N-(t-butyl 6-(4,4-dimethyl-2,6-dioxocyclohexylidene)-hexanoate-6-yl) 4-aminobenzyl alcohol (500 mg, 1.16 mmol) and trichloroacetonitrile (503 mg, 3.49 mmol) in CH$_2$Cl$_2$ (5 ml) was stirred at 0° C. and 1,8-diazabicyclo(5.4.0)undec-7-ene (5 mg, 0.03 mmol) added. The reaction mixture was stirred at 0° C. for 90 minutes, at room temperature for 2 h, then evaporated. The residue was purified by chromatography using EtOAc/hexane 1:1 as the mobile phase to give N-(t-butyl 6-(4,4-dimethyl-2,6-dioxocyclohexylidene)-hexanoate-6-yl) 4-aminobenzyl trichloroacetimidate (580 mg, 87%);

$R_f$ 0.41 (EtOAc/hexane 1:1 v/v); FAB MS C$_{27}$H$_{35}$Cl$_3$N$_2$O$_5$ (573.94) m/z (%) 595 [M+Na]$^+$ (100), 753 [M+H]$^+$ (40), 515 (39), 430 (54).

EXAMPLE 26
Synthesis of a Fully Protected Sugar (Sugar-Linker Bond is not at the Glycosidic Position)-Ddh-Aminobenzyl t-Butyl Ester Conjugate Via Trichloroacetimidate Activation (FIG. 4)
26 Benzyl 2-acetamido-3-O-acetyl-6-O-benzyl-2-deoxy-4-O-[N-(t-butyl 6-(4,4-Dimethyl-2,6-dioxocyclo-hexylidene)-hexanoate-6-yl) 4-Aminobenzyl]-α-D-glucopyranoside N-(t-Butyl 6-(4,4-dimethyl-2,6-dioxocyclo-hexylidene)-hexanoate-6-yl) 4-aminobenzyl trichloro-acetimidate (400 mg, 0.70 mmol) was added at 20° C. under nitrogen to a solution of Benzyl 2-acetamido-3-O-acetyl-6-O-benzyl-2-deoxy-α-D-glucopyranoside (155 mg, 0.35 mmol) in CH$_2$Cl$_2$ (6 ml). Trifluoromethanesulphonic acid in ether (0.1 M, 0.06 ml) was added and the mixture was stirred for 30 min at 20° C. The reaction was stopped with 5% NaHCO$_3$ solution (0.25 ml).After filtration of the mixture and evaporation of the filtrate, the crude residue was purified by chromatography using EtOAc/hexane 2:1 v/v as the mobile phase to give Benzyl 2-acetamido-3-O-acetyl-6-O-benzyl-2-deoxy-4-O-[N-(t-butyl 6-(4,4-dimethyl-2,6-dioxocyclo-hexylidene)-hexanoate-6-yl) 4-aminobenzyl]-α-D-glucopyranoside (210 mg, 71%).

$R_f$ 0.37 (EtOAc/hexane 2:1 v/v); FAB MS C$_{49}$H$_{62}$N$_2$O$_{11}$ (855.01) m/z (%) 877 [M+Na]$^+$ (100), 855 [M+H]$^+$ (35), 797 (73).

EXAMPLE 27
Synthesis of a Fully Protected Glycoside (Sugar-Linker Bond at the Glycosidic Position)-Ddh-Aminobenzyl Linker-Resin Via Trichloroacetimidate Activation (FIG. 4)
27 [N-(6-(4,4-Dimethyl-2,6-dioxocyclohexylidene)-hexanoic Acid-6-yl) 4-Aminobenzyl] 2,3,4,6-tetra-O-acetyl-β-D-glucopyranoside MBHA Resin Conjugate N-(t-Butyl 6-(4,4-dimethyl-2,6-dioxocyclo-hexylidene)-hexanoate-6-yl) 4-aminobenzyl trichloroacetimidate (400 mg, 0.70 mmol) was added at 20° C. under nitrogen to a solution of 2,3,4,6-tetra-O-acetyl-β-D-glucopyranose (121 mg, 0.35 mmol) in CH$_2$Cl$_2$ (6 ml). Trifluoromethanesulphonic acid in ether (0.1 M, 0.06 ml) was added and the mixture was stirred for 30 min at 20° C. The reaction was stopped with 5% NaHCO$_3$ solution (0.25 ml). After filtration of the mixture, the filtrate was evaporated. The unpurified residue was taken up in CH$_2$Cl$_2$/TFA mixture (1:1) (5 ml), stirred at room temperature for 1 h and evaporated. The resulting acid was dissolved in CH$_2$Cl$_2$ (5 ml), N,N'-diisopropylcarbodiimide (128 mg, 1 mmol) added, and the mixture was gently agitated with MBHA resin (100 mg) (swelled in DMF for 20 min.) for 30 min.

EXAMPLE 28
Synthesis of a Fully Protected Glycoside (Sugar—Linker Bond is at the Glycoside Position)-Ddh-Aminobenzyl Benzyl Ester Conjugate Via DMTST Promoted Glycosylation (see 26, FIG. 4)

28 [N-[Benzyl (6-(4,4-Dimethyl-2,6-dioxocyclohexylidene)-hexanoate]-6-yl 4-Aminobenzyl]-2,3,4,6-tetra-O-acetyl-β-D-glucopyranoside A mixture of N-[Benzyl (6-(4,4-dimethyl-2,6-dioxocyclohexylidene)-hexanoate]-6-yl 4-aminobenzyl alcohol (500 mg, 1.08 mmol), methyl 2,3,4,6-tetra-O-acetyl-1-thio-β-D-glucopyranoside (400 mg, 1.08 mmol) in $CH_2Cl_2$ (10 ml) was stirred at room temperature and DMTST (835 mg, 3.24 mmol) added. The solution was stirred at room temperature for 1 h and washed with saturated $NaHCO_3$ solution (3 ml), dried over $MgSO_4$ and evaporated. The residue was purified by chromatography using hexane/EtOAc 1:1 v/v as the mobile phase to give [N-[Benzyl (6-(4,4-dimethyl-2,6-dioxocyclohexylidene)-hexanoate]-6-yl 4-aminobenzyl]-2,3,4,6-tetra-O-acetyl-β-D-glucopyranoside (610 mg, 75%).

$R_f$ 0.47 (hexane/EtOAc 1:1 v/v); FAB MS $C_{42}H_{51}NO_{14}$ (793.83) m/z (%) 816 [M+Na]$^+$ (100), 794 [M+H]$^+$ (25), 702 (66).

EXAMPLE 29
Synthesis of a Fully Protected Glycoside (Sugar-Linker Bond is at the Glycosidic Position)-Ddh-Aminobenzyl Linker-Resin Conjugate Via DIPCDI Activation (see 27, FIG. 4)

29 [N-(6-(4,4-Dimethyl-2,6-dioxocyclohexylidene)-hexanoic Acid-6-yl) 4-Aminobenzyl]-2,3,4,6-tetra-O-acetyl-β-D-glucopyranoside MBHA Resin Conjugate

[N-[Benzyl (6-(4,4-dimethyl-2,6-dioxocyclohexylidene)-hexanoate]-6-yl 4-aminobenzyl]-2,3,4,6-tetra-O-acetyl-β-D-glucopyranoside (500 mg, 0.63 mmol) was hydrogenated over Pd/C (10%) (200 mg) in MeOH (20 ml) at room temperature for 10 hours. The catalyst was filtered off and the filtrate was evaporated. The residue was dissolved in $CH_2Cl_2$ (5 ml), N,N'-diisopropylcarbodiimide (128 mg, 1 mmol) added, and the mixture was gently agitated with MBHA resin (200 mg) (pre-swelled in DMF for 20 min.) for 30 min.

EXAMPLE 30
Synthesis of a Partially Protected Glycosyl Amine-Ddh Conjugate Using Ddh-OH t-Butyl Ester in Solution (see 22, FIG. 3)

30 N-(6-(4,4-Dimethyl-2,6-dioxocyclohexylidene)-hexanoic Acid-6-yl) 2,3,6-tri-O-benzyl-β-D-galactopyranosyl Amine A mixture of t-butyl 6-hydroxy-6-(4,4-dimethyl-2,6-dioxocyclohexylidene)-hexanoate (400 mg, 1.23 mmol) and 2,3,6-tri-O-benzyl-β-D-galactopyranosyl amine (276 mg, 0.61 mmol) in abs. EtOH (10 ml) was stirred under reflux for 2 h. The reaction mixture was evaporated. The residue was taken up in $CH_2Cl_2$/TFA mixture (1:1) (10 ml) and stirred at room temperature for 1 h. The reaction mixture was evaporated and purified by chromatography using $CHCl_3$/MeOH 10:0.1 v/v as the mobile phase to give N-(6-(4,4-dimethyl-2,6-dioxocyclohexylidene)-hexanoic acid-6-yl) 2,3,6-tri-O-benzyl-β-D-galactopyranosyl amine (280 mg, 73%).

$R_f$ 0.34 ($CHCl_3$/MeOH 10:0.1 v/v) FAB MS $C_{37}H_{43}NO_7$ (613.41) m/z (%) 649 [M+2Na]$^+$ (34), 626 [M+Na]$^+$ (100), 614 [M+H]$^+$ (65).

EXAMPLE 31
Synthesis of a Fully Protected Glycosyl Amine-Ddh-Resin Conjugate Where the Resin Coupling is the Final Step (FIG. 3)

31 N-(6-(4,4-Dimeethyl-2,6-dioxocyclohexylidene)-hexanoic Acid-6-yl) 2,3,4,6-Tetra-O-acetyl-β-D-glucopyranosyl Amine-MBHA Conjugate MBHA resin (Subst. ratio:0.42 mmol/g) (200 mg) bearing a total amine functionality of 0.084 mmol was swollen in DMF for 20 min. The resin was then washed with fresh DMF and N-(6-(4,4-dimethyl-2,6-dioxocyclohexylidene)-hexanoic acid-6-yl) 2,3,4,6-tetra-O-acetyl-β-D-glucopyranosyl amine (200 mg, 4 equiv.) and N,N'-diisopropylcarbodiimide (53 μl,4 equiv.) were added in DMF (5 ml) and the resin gently agitated for 30 min. The TNBS test was faintly positive so using the above conditions, a double coupling was performed, this time producing a negative TNBS test result. The resin was washed with DMF, methanol and finally ether. The resin was then allowed to dry in vacuum over KOH overnight.

EXAMPLE 32
Synthesis of a Fully Protected Sugar (Sugar—Linker Bond is Not at the Glycosidic Position)-Ddh-Resin Conjugate Where the Resin Coupling is the Final Step (see 27, FIG. 4)

32 Benzyl 2-Acetamido-3-O-acetyl-6-O-benzyl-2-deoxy-4-O-[N-(6-(4,4-Dimethyl-2,6-dioxocyclohexyl-idene)-hexanoic Acid-6-yl) 4-Aminobenzyl]-α-D-glucopyranoside-MBHA Resin Conjugate Benzyl 2-acetamido-3-O-acetyl-6-O-benzyl-2-deoxy-4-O-[N-(t-butyl 6-(4,4-dimethyl-2,6-dioxocyclohexylidene)-hexanoate-6-yl) 4-aminobenzyl]-α-D-glucopyranoside (290 mg, 0.33 mmol) was dissolved in $CH_2Cl_2$/TFA mixture (1:1) and stirred at room temperature for 1 h. The reaction mixture was evaporated, and procedure 31 was used to bind the compound to the MBHA resin.

Figure 10:
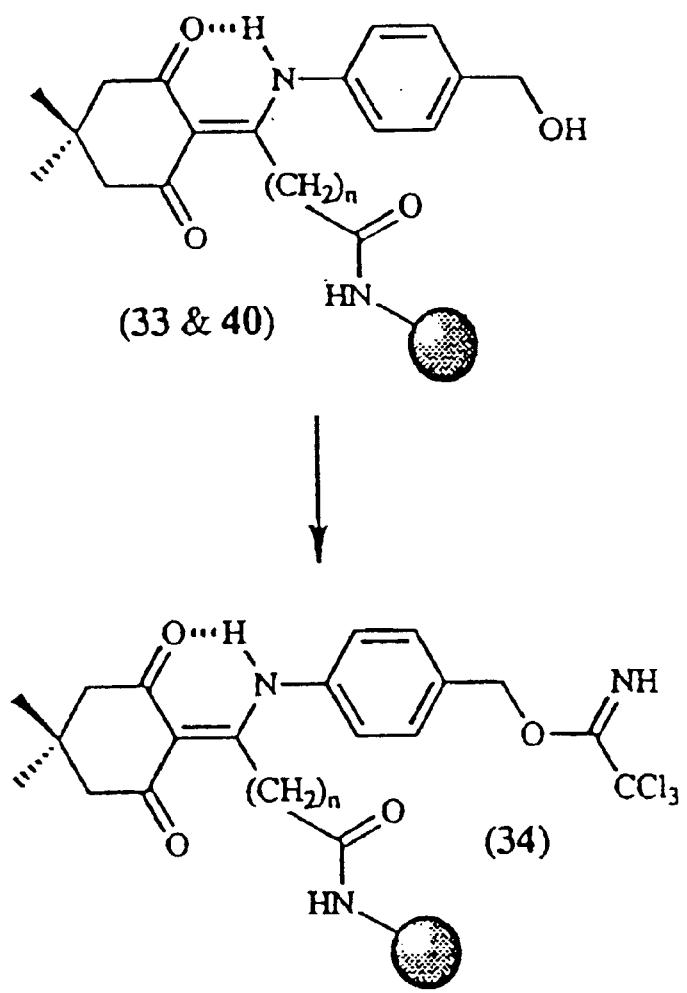
FIG. 10 shows the trichloroacetimidate activation of the 4-aminobenzyl modified linker.

EXAMPLE 33
Synthesis of Ddh-Aminobenzyl Linker-Resin Conjugate With Selective Resin Coupling (Unprotected Hydroxyl Group is Present on the Linker) (FIG. 10)

33 N-(6-(4,4-Dimethyl-2,6-dioxocyclohexylidene)-hexanoic Acid-6-yl) 4-Amino-benzylalcohol-MBHA Resin Conjugate MBHA resin (100 mg) bearing a total amine functionality of 0.042 mmol was swelled in DMF for 20 min. The resin was then washed with fresh DMF and N-(6-(4,4-dimethyl-2,6-dioxocyclohexylidene)-hexanoic acid-6-yl) 4-aminobenzyl alcohol (63 mg, 4 equiv.) and 1-isobutyloxy-carbonyl-2-isobutyloxy-1,2-dihydroquinoline (EEDQ) (51 mg, 4 equiv.) were added in DMF (5 ml) and the resin gently agitated for 24 h. The TNBS test was faintly positive so using the above conditions, a double coupling was performed, this time producing a negative TNBS test result. The resin was washed with DMF (5×10 ml).

EXAMPLE 34
Synthesis of Ddh-Aminobenzyl Trichloroacetimidate Activated Linker-Resin Conjugate When the Activation Takes Place on the Resin (FIG. 10)

34 N-(6-(4,4-Dimethyl-2,6-dioxocyclohexylidene)-hexanoate-6-yl) 4-Aminobenzyl Trichloroacetimidate-MBHA Resin Conjugate Resin from Example 33 was treated with trichloroacetonitrile (50 mg, 0.33 mmol) in $CH_2Cl_2$ (1 ml) was stirred at 0° C. and 1,8-diazabicyclo(5.4.0)undec-7-ene (1 mg, 0.003 mmol) added. The reaction mixture was stirred at 0° C. for 90 minutes, at room temperature for 2 h, then the resin was filtered off and washed with DMF (5×10 ml).

EXAMPLE 35
Synthesis of a Fully Protected Sugar (Sugar-Linker Bond is Not at the Glycosidic Position)-Ddh-Resin Conjugate When the Sugar Coupling is the Final Step (see 32, FIG. 4)

35 Benzyl 2-Acetamido-3-O-acetyl-6-O-benzyl-2-deoxy-4-O-[N-(6-(4,4-Dimethyl-2,6-dioxocyclo-hexylidene)-hexanoic Acid-6-yl) 4-Aminobenzyl]-α-D-glucopyranoside-MBHA Resin Conjugate Resin from Example 34 was added at room temperature to a solution of Benzyl 2-acetamido-3-O-acetyl-6-O-benzyl-2-deoxy-α-D-glucopyranoside (75 mg, 0.16 mmol) in $CH_2Cl_2$ (1 ml). Trifluoromethanesulphonic acid in ether (0.1 M, 60 µl) was added and the mixture was stirred for 30 min. The reaction was stopped with triethylamine (120 µl) and washed with DMF (5×10 ml).

EXAMPLE 36
First Step of the Solid Phase Synthesis of the Resin-Ddh- or DdH-Aminobenzyl-Linker (FIG. 3)
36 Adipic acid-MBHA Resin Conjugate MBHA resin (1.0 g) bearing a total amine functionality of 0.42 mmol was swelled in DMF for 20 min. The resin was then treated with a mixture of adipic acid (1.41 g, 10 mmol) and N,N'-diisopropylcarbodiimide in $CH_2Cl_2$ (10 ml) for 60 min. A second coupling was performed in DMF to get a negative ninhydrin test. The resin was washed with DMF (5×10 ml).

EXAMPLE 37
Second Step of the Solid Phase Synthesis of the Resin-Ddh- or DdH-Aminobenzyl-Linker (FIG. 3)
37 6-Hydroxy-6-(4,4-Dimethyl-2,6-dioxocyclo-hexylidene)-hexanoic Acid-MBHA Resin Conjugate To the resin from Example 36 a mixture of 5,5-dimethyl-1,3-cyclohexanedione (280 mg, 2.0 mmol), N,N'-dicyclohexylcarbodiimide (283 mg, 2.00 mmol) and 4-dimethylaminopyridine (244 mg 2.00 mmol) was added in $CH_2Cl_2$ (10 ml) and stirred at room temperature for 18 h. The resin was washed with DMF (5×10 ml).

EXAMPLE 38
Solid Phase Synthesis of a Fully Protected Glycosyl Amine-Ddh-Resin Conjugate (see 31, FIG. 3)
38 N-(6-(4,4-Dimethyl-2,6-dioxocyclohexylidene)-hexanoic Acid-6-yl) 2,3,4,6-Tetra-O-acetyl-β-D-glucopyranosyl Amine-MBHA Resin Conjugate The resin from Example 37 was reacted with 2,3,4,6-tetra-O-acetyl-β-D-glucopyranosyl amine (712 mg, 2.00 mmol) in DMF (5 ml) at room temperature for 2 days. The resin was washed with DMF (5×10 ml).

EXAMPLE 39
Solid Phase Synthesis of a Partially Protected Glycosyl Amine-Ddh-Resin Conjugate (FIG. 3)
39 N-(6-(4,4-Dimethyl-2,6-dioxocyclohexylidene)-hexanoic Acid-6-yl) 2,3,6-Tri-O-benzyl-β-D-galactopyranosyl Amine-MBHA Resin Conjugate The resin from Example 37 was reacted with 2,3,6-tri-O-benzyl-β-D-galactopyranosyl amine (900 mg, 2.00 mmol) in abs. EtOH under reflux for 2 h. The resin was washed with DMF (5×10 ml).

EXAMPLE 40
Solid Phase Synthesis of Ddh-Aminobenzyl Linker-Resin Conjugate (see 33, FIG. 10)
40 N-(6-(4,4-Dimethyl-2,6-dioxocyclohexylidene)-hexanoic Acid-6-yl) 4-Amino-benzylalcohol-MBHA Resin Conjugate A mixture of resin from Example 37 and 4-aminobenzyl alcohol (246 mg, 2.00 mmol) in abs. EtOH was stirred under reflux for 2 h, then washed with DMF (5×10 ml).

EXAMPLE 41
Cleavage of a Fully Protected Glycosyl Amine-Ddh-Resin Conjugate Affording Fully Protected Glycosyl Amine (FIG. 11)
41 Cleavage of N-(6-(4,4-Dimethyl-2,6-dioxocyclo-hexylidene)-hexanoic Acid-6-yl) 2,3,4,6-Tetra-O-acetyl-β-D-glucopyranosyl amine-MBHA Resin Conjugate by $NH_3$ Treatment.

Resin from Example 38 (10 mg) was treated with saturated $NH_3$/MeOH solution (0.2 ml) at room temperature for 5 min. The resin was filtered off, the filtrate was evaporated, giving 2,3,4,6-tetra-O-acetyl-β-D-glucopyranosyl amine in quantitative yield.

Figure 11:
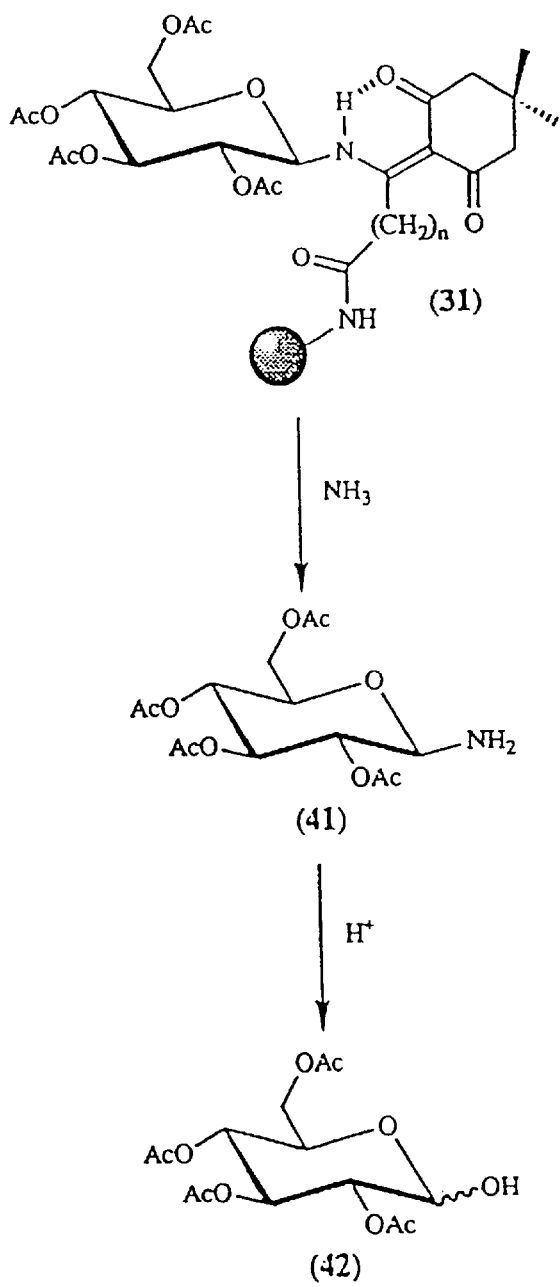
FIG. 11 shows ammonia-mediated cleavage of the aminoglycoside with post-cleavage acidification to generate the free carbohydrate.

EXAMPLE 42
Cleavage of a Fully Protected Glycosyl Amine-Ddh-Resin Conjugate Affording Fully Protected Reducing Sugar
42 Cleavage of N-(6-(4,4-Dimethyl-2,6-dioxocyclo-hexylidene)-hexanoic Acid-6-yl) 2,3,4,6-Tetra-O-acetyl-β-D-glucopyranosyl Amine-MBHA Resin Conjugate by $NH_3$ treatment, Affording a Reducing Carbohydrate Derivative (FIG. 11).

Resin from Example 38 (10 mg) was treated with saturated $NH_3$/MeOH solution (0.2 ml) at room temperature for 5 min. The resin was filtered off, the filtrate was evaporated. The residue was dissolved in the mixture of acetone/water 10:1 v/v (0.2 ml), acidified with acetic acid (20 µl) and stirred at room temperature for 1 h. The solution was evaporated giving 2,3,4,6-tetra-O-acetyl-β-D-glucopyranose in quantitative yield.

Figure 12:
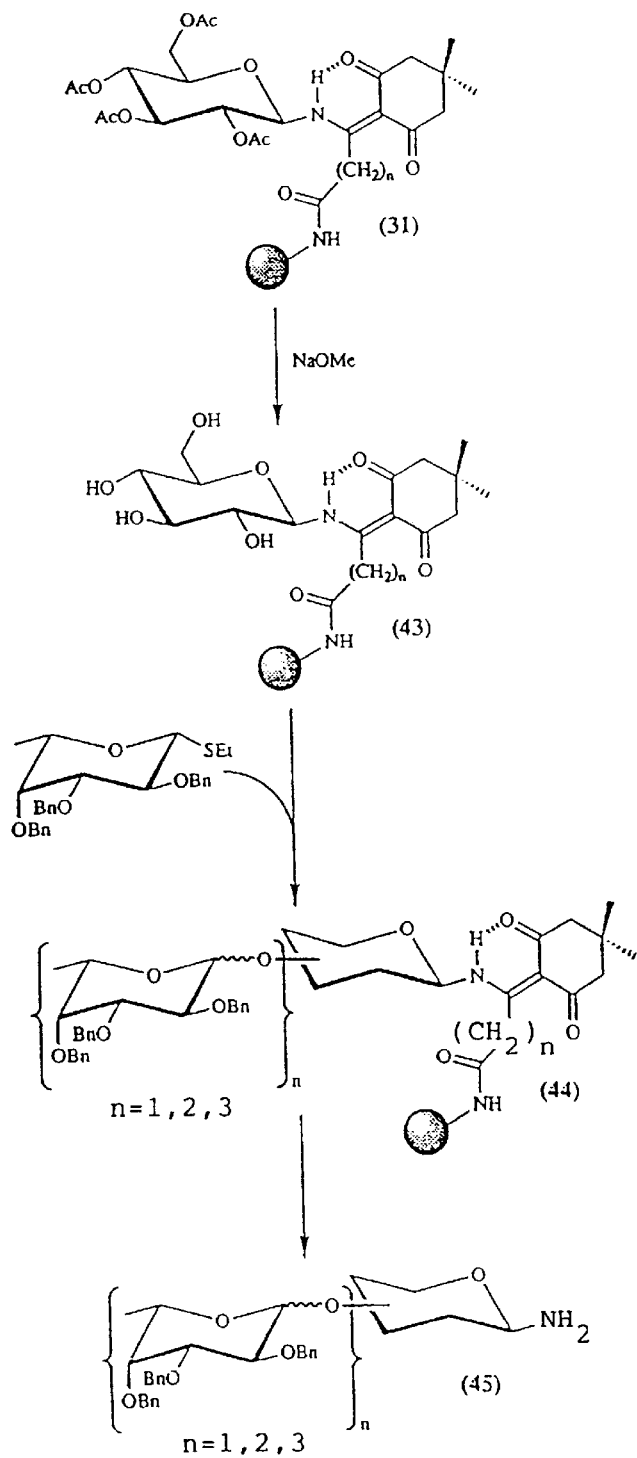
FIG. 12 shows a specific example of the general strategy for oligosaccharide synthesis employing a thiogycoside as the sugar donor.

EXAMPLE 43
Carbohydrate Deprotection of the Fully Protected Sugar-Ddh Linker-Resin Conjugate (FIG. 12)
43 N-(6-(4,4-Dimethyl-2,6-dioxocyclohexylidene)-hexanoic Acid-6-yl) β-D-glucopyranosyl amine-MBHA Resin Conjugate The resin from Example 38 was gently agitated with sodium methoxide (200 mg, 3.70 mmol) in abs. MeOH (5 ml) at room temperature for 1 h. The resin was washed with abs. MeOH (5×10 ml), DMF(5×10 ml), ether (5×10 ml) and dried under high vacuum for 1 h, giving the resin-bonded unprotected β-D-glucopyranosyl amine. A sample of resin (5 mg) was cleaved by $NH_3$/MeOH (Example 41), and the resulting product was analyzed by TLC and mass spectometry, proving the quantitative deprotection.

EXAMPLE 44
Synthesis of a Library of Di-, Tri- and Tetrasaccharides on a Solid Support (FIG. 12)
44 A mixture of mono-, di- and tri-O-(2,3,4-tri-O-benzyl α,β-L-fucopyranosyl) (1→2), (1→3), (1→4), (1→6)-[N-(6-(4,4-Dimethyl-2,6-dioxocyclo-hexylidene)-hexanoic Acid-6-yl)] β-D-glucopyranosyl Amine-MBHA Resin Conjugate A mixture of resin from Example 43 and ethyl 2,3,4-tri-O-benzyl-1-thio-βL-fucopyranoside (950 mg, 2 mmol) in dry $CH_2Cl_2$ (10 ml) was treated with dimethyl-(methylthio)-sulphonium trifluoromethanesulphonate (DMTST) (1.50 g, 5.81 mmol) at room temperature for 1 h. The resin was washed with dry $CH_2Cl_2$ (5×10 ml).

EXAMPLE 45
Cleavage of a Library of Di-, Tri- and Tetrasaccharides from the Resin Affording Glycosyl Amine of Oligosaccharides (FIG. 12)
45 A mixture of mono-, di- and tri-O-(2,3,4-Tri-O-benzyl α,β-L-fucopyranosyl) (1→42), (1→43), (1→4), (1→6)-β-D-glucopyranosyl Amine The resin from Example 44 was treated with $NH_3$/MeOH (10 ml) for 5 min. The resin was filtered off, and the filtrate was evaporated giving a mixture of disaccharides, trisaccharides, and tetrasaccharides.

FAB MS disaccharides $C_{33}H_{41}NO_9$ (595.66), trisaccharides $C_{60}H_{69}NO_{13}$ (1012.16), tetrasaccharides $C_{87}H_{97}NO_{17}$ (1429.66) (m/z (%) 618 [$M_{di}$+Na]$^+$ (41), 596 [$M_{di}$+H]$^+$ (57), 1034 [$M_{tri}$+Na]$^+$ (56), 1012 [$M_{tri}$+H]$^+$ (100), 1450 [$M_{tetra}$+Na]$^+$ (8), 1428 [$M_{tetra}$+H]$^+$ (10).

Figure 13:
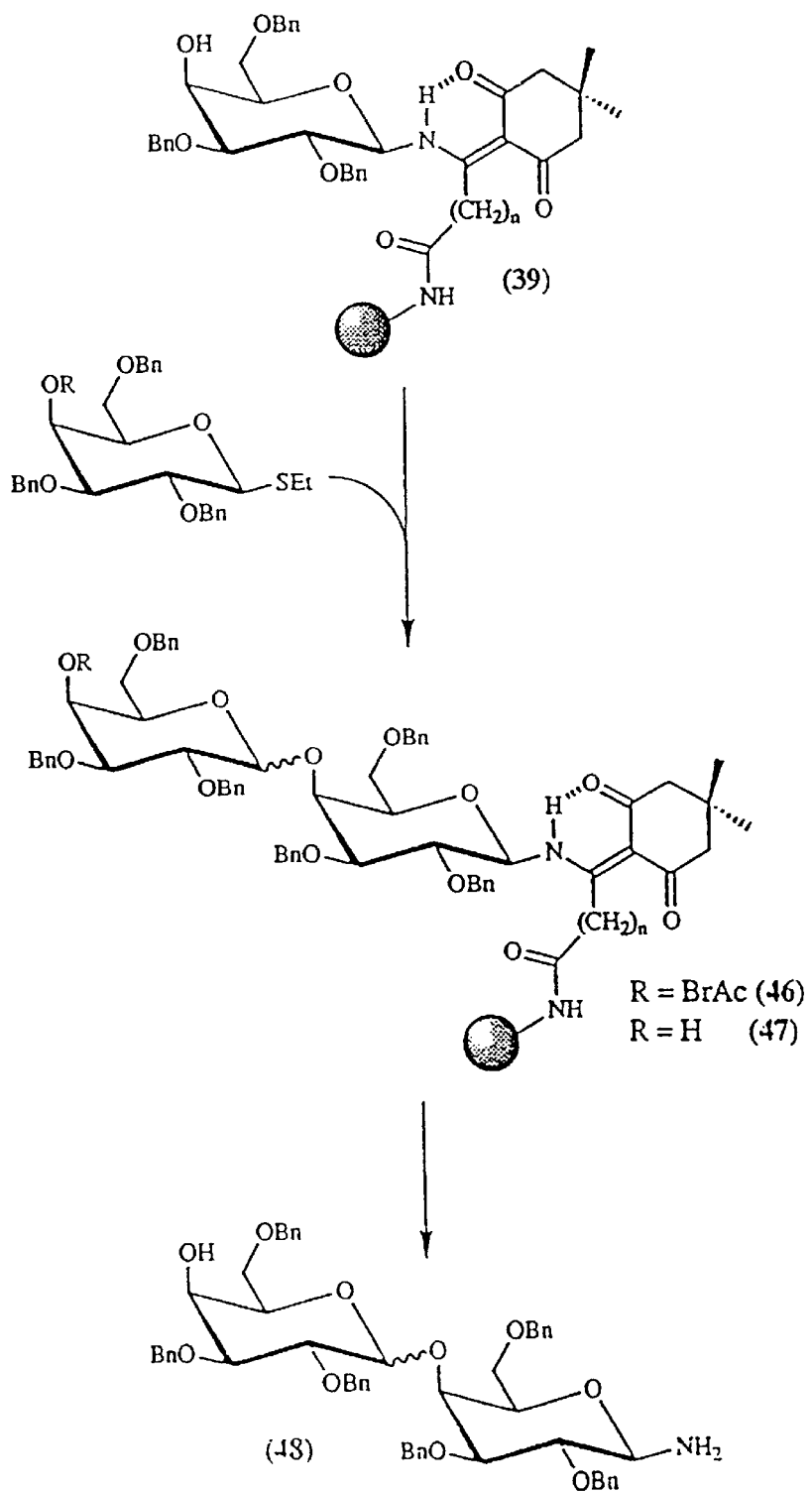
FIG. 13 shows another specific example of the general strategy for oligosaccharide synthesis employing a thiogycoside as the sugar donor.

EXAMPLE 46
Synthesis of a Second Sugar-Glycosyl Amine-Ddh Linker-Resin Conjugate (FIG. 13)
46 O-(2,3,6-Tri-O-benzyl-4-O-bromoacetyl-α,β-D-galactopyranosyl) (1→4)-[N-(6-(4,4-Dimethyl-2,6-dioxocyclobexylidene)-hexanoic Acid-6-yl)] 2,3,6-tri-O-benzyl-β-D-galactopyranosyl Amine-MBHA Resin Conjugate A mixture of resin from Example 39 and ethyl 2,3,6-tri-O-benzyl-4-O-bromoacetyl-1-thio-β-D-galactopyranoside (1.25 g, 2 mmol) in dry $CH_2Cl_2$ (10 ml) was treated with dimethyl(methylthio)sulphonium trifluoromethanesulphonate (DMTST) (1.50 g, 5.81 mmol) at room temperature for 1 h. The resin was washed with dry $CH_2Cl_2$ (5×10 ml).

EXAMPLE 47
Selective Deprotection of the Second Sugar-Glycosyl Amine-Ddh Linker-Resin Conjugate (FIG. 13)
47 O-(2,3,6-Tri-O-benzyl-α,β-D-galacto-pyranosyl) (1→4)-(N-(6-(4,4-Dimethyl-2,6-dioxocyclohexylidene)-hexanoic Acid-6-yl)] 2,3,6-Tri-O-benzyl-O-D-galactopyranosyl Amine-MBHA Resin Conjugate The resin from Example 46 was gently agitated with sodium methoxide (200 mg, 3.70 mmol) in abs. MeOH (5 ml) at room temperature for 1 h. The resin was washed with abs. MeOH (5×10 ml), DMF(5×10 ml), ether (5×10 ml) and dried under high vacuum for 1 h, giving the resin bonded partially unprotected disaccharide. A sample of resin (5 mg) was cleaved by $NH_3$/MeOH (Example 41) and the resulting product was analyzed by TLC and mass spectometry, proving the quantitative deprotection.

EXAMPLE 48
Cleavage of a Second Sugar-Glycosyl Amine-Ddh Linker-Resin Conjugate Affording a Glycosyl Amine of a Disaccharide (FIG. 13)
48 O-(2,3,6-Tri-O-benzyl-α,β-D-galacto-pyranosyl) (1→4)-2,3,6-tri-O-benzyl-β-D-galactopyranosyl Amine The resin from Example 47 was treated with $NH_3$/MeOH (10 ml) for 5 min. The resin was filtered off, and the filtrate was evaporated giving an anomeric mixture of disaccharides. FAB MS $C_{54}H_{59}NO_{10}$ (882.01) (m/z (%) 904 [M+Na]$^+$ (100), 880 [M+H]$^+$ (41).

Figure 14:
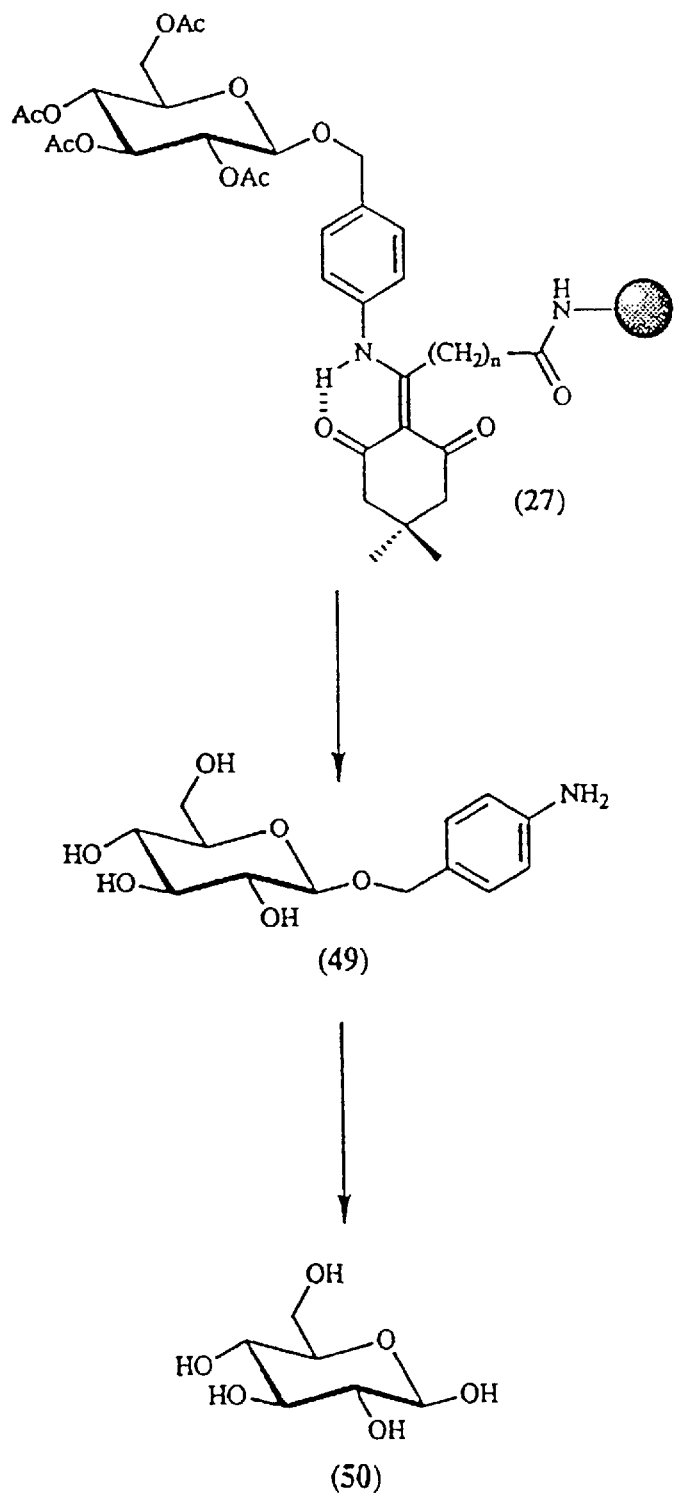
FIG. 14 shows the cleavage of a monosaccharide bound to the 4-aminobenzyl modified linker.

EXAMPLE 49
Cleavage of a Carbohydrate-Ddh-Aminobenzyl Linker-Resin Conjugate Affording an Aminobenzyl Protected Carbohydrate (FIG. 14)
49 4-Aminobenzyl β-D-glucopyranoside The resin from Example 29 was treated with $NH_3$/MeOH (5 ml) overnight. The resin was filtered off, and the filtrate was evaporated giving 4-aminobenzyl β-D-glucopyranoside.

$R_f$ 0.55 ($CHCl_3$/MeOH/$H_2O$ 10:4:0.5 v/v/v); FAB MS $C_{13}H_{19}NO_5$ (269.28) m/z (%) 402 [M+Cs]$^+$ (25), 292 [M+Na]$^+$ (50), 270 [M+H]$^+$ (18).

EXAMPLE 50
Deprotection of 4-Aminobenzyl Protected Carbohydrate (FIG. 14)
50 β-D-Glucopyranose 4-Aminobenzyl P-D-glucopyranoside (110 mg, 0.40 mmol) was hydrogenated over Pd/C (10%) (50 mg) in MeOH (5 ml) at room temperature for 4 hours. The catalyst was filtered off and the filtrate was evaporated affording D-glucose in quantitative yield.

Figure 15:
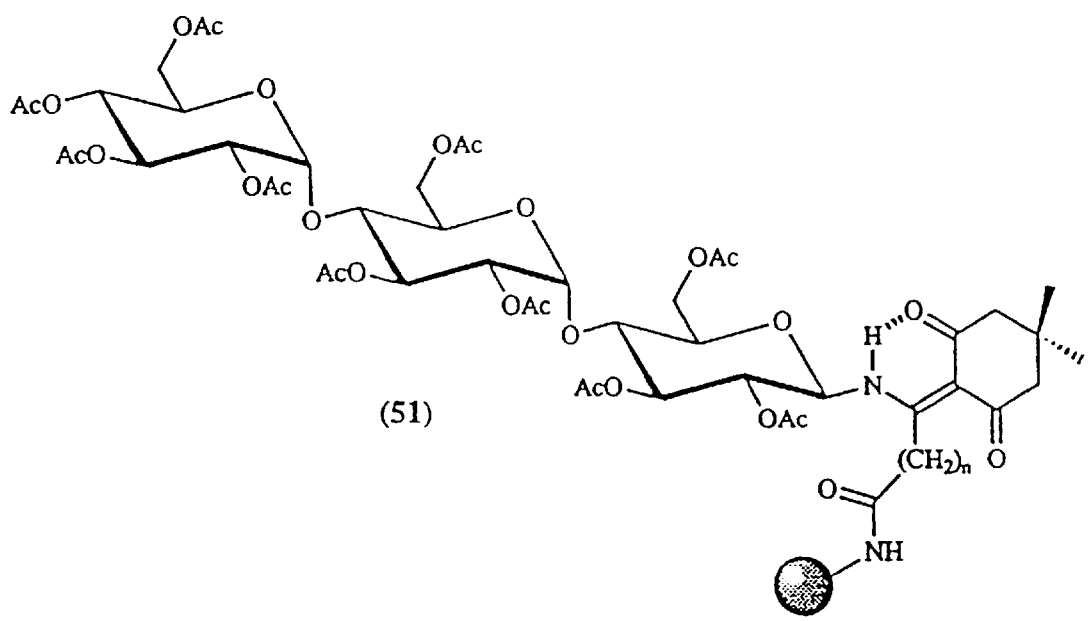
FIG. 15 shows an example of a resin-bound fully protected trisaccharide.

EXAMPLE 51
Immobilization of an Oligosaccharide (FIG. 15)
51 O-[O-(2,3,4,6-Tetra-O-acetyl-β-D-glucopyranosyl (1→4))-2,3,6-tri-O-acetyl-β-D-glucopyranosyl (1→4)]-2,3,6-tri-O-acetyl-β-D-glucopyranosyl Amine using 6-hydroxy-6-(4,4-dimethyl-2,6-dioxocyclohexylidene)-hexanoic Acid-MBHA Resin Conjugate The resin from Example 37 was reacted with O-(O-(2,3,4,6-tetra-O-acetyl-β-D-glucopyranosyl (1→4))-2,3,6-tri-O-acetyl-β-D-glucopyranosyl(1→4)]-2,3,6-tri-O-acetyl-β-D-glucopyranosyl amine (1.80 g, 2.00 mmol) in DMF (5 ml) at room temperature for 2 days. The resin was washed with DMF (5×10 ml).

Figure 16:
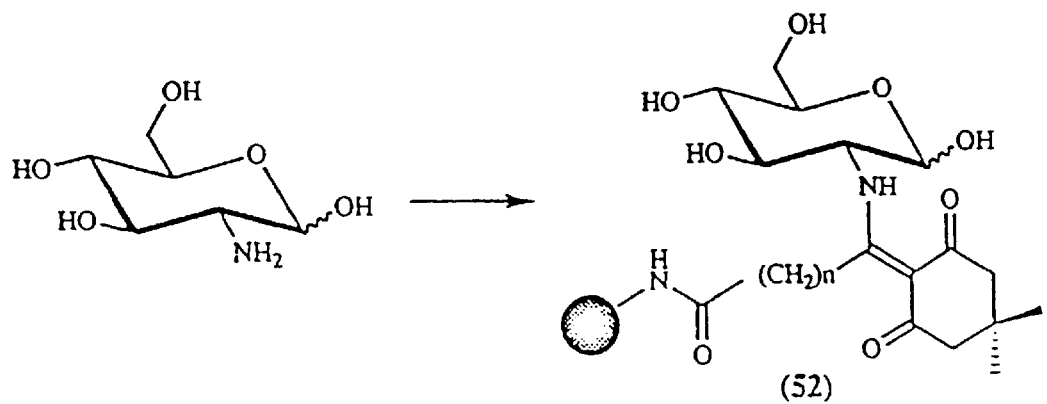
FIG. 16 shows the immobilisation of an unprotected amino sugar.

EXAMPLE 52
Synthesis of an Aminosugar-Ddh-resin Conjugate (FIG. 16)
52 N-(6-(4,4-Dimethyl-2,6-dioxocyclohexlidene)-hexanoic Acid-6-yl) D-glucosamine-MBHA Resin Conjugate A mixture of resin from Example 37 and glucosamine (350 mg, 2 mmol) in DMF (20 ml) was stirred at room temperature for 2 days. The resin was filtered off, washed with DMF/$H_2O$ 4:1 (5×10 ml), DMF 5×10 ml, MeOH (5×10), ether (5×10 ml), and dried under high vacuum overnight.

It will be apparent to the person skilled in the art that while the invention has been described in some detail for the purposes of clarity and understanding, various modifications and alterations to the embodiments and methods described herein may be made without departing from the scope of the inventive concept disclosed in this invention.

References cited herein are listed on the following pages, and are incorporated by this reference.

REFERENCES

Adinolfi, M., Barone, G., De Napoli, L., Iadonisi, A. and Piccialli, G.

Tetrahedron Lest., 1936 37 5007.

Bannwarth, W., Huebscher, J. and Barner, R.

Bioorganic and Med. Chem. Lett., 1996 6 1525.

Boren, T. et al. Science, 1993 262 1892.

Bycroft, B. W., Chan, W. C., Chhabra, S. R. and Hone, N. D. J. Chem. Soc., Chem. Commun., 1993 778.

Chan, W. C., Bycroft, B. W., Evans, D. J. and White, P. D. J. Chem. Soc., Chem. Coimmun., 1995 2209.

Douglas, S. P., Whitfield, D. M. and Krepinsky, J. J. J. Am. Chem. Soc., 1995, 117 2116.

Fisher, J. F. et al. J. Med. Chem., 1991 34 3140.

Frechet, J. M. and Schuerch, C. J. Am. Chem. Soc., 1971 93 492.

Frechet, J. M. and Schuerch. C. J. Am. Chem. Soc., 1972 94 604.

Gambaryan, A. S. et al. FEBS Lett., 1995 366 57.

Guthrie, R. D., Jenkins, A. D. and Stehlicek, J. J. Am. Chem. Soc., 1971 (c) 2690.

Guthrie, R. D., Jenkins, A. D. and Roberts, J. A. F. J. Chem. Soc., Perkin Trans. 1, 1973 1 2441.

Lasky, L. A. Science, 1992 258 964.

Lee, Y. C. in Carbohydrate Recognition in Cellular Function (G Block and S. Harnett, Eds.), John Wiley & Sons, 1989 80.

Merrifield, R. B. J. Am. Chem. Soc., 1963 85 2149.
Rademann, J. and Schmidt, R. R. Tetrahedron Lett., 1996 37 3989.
Randolph, J. T., McClure, K. F. and Danishefsky, S. J. J. Am. Chem. Soc., 1995 117 5712.
Roberge, J. Y., Beebe, X. and Danishefsky, S. J. Science, 1995 269 202.
Rodriguez, R. E. et al. Neurosci. Lett., 1989 101 89.
Varki, A. Glycobiology, 1993 3 97.
Yan, L., Taylor, C. M., Goodnow Jr., R. and Kahne, D. J. Am. Chem. Soc., 1994 116 6953.

What is claimed is:

1. A linker compound comprising functional groups suitable to attach a primary amine to a resin via covalent bonds that are stable to conditions of oligosaccharide synthesis and cleavage, said compound having formula III

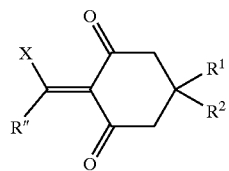

in which

X is OH;

$R^1$ is hydrogen or $C_{1-4}$ alkyl;

$R^2$ is hydrogen or $C_{1-4}$ alkyl; and

R" is an alkyl, substituted alkyl, aryl, substituted aryl, cycloalkyl, or substituted cycloalkyl spacer group that comprises a functionality capable of reacting with a functionalized resin.

2. The compound of claim 1, in which both $R^1$ and $R^2$ are methyl.

3. The compound of claim 1, in which the functionality on R" is a carboxyl group.

4. The compound of claim 1, which is 6-hydroxy-6-(4,4-dimethyl-2,6-dixocyclohexylidene)-hexanoic acid or an ester thereof.

5. The compound of claim 4, in which the ester is a benzyl, methyl or t-butyl ester.

6. A method of synthesis of the linker compound of claim 1, in which said method comprises C-acylation of a 1,3-dioxocyclohexane compound with a dicarboxylic acid or dicarboxylic acid anhydride.

7. The method of claim 6, wherein said method further comprises reacting the product of the C-acylation reaction with 4-aminobenzyl alcohol, to form the 4-aminobenzyl derivative.

8. The method of claim 6, in which the dicarboxylic acid is mono-protected by ester formation.

9. The method of claim 6, in which the C-acylation reaction is activated with carbodiimide and catalyzed by N,N'-dimethylaminopyridine.

10. The method of claim 6, in which the 1,3-dioxocycloalkane compound is 5,5-dimethyl-1,3-cyclohexanedione.

11. The method of claim 6, in which said dicarboxylic acid is adipic acid or glutaric acid or the anhydride thereof.

12. A resin-linker support for solid-phase synthesis of oligosaccharides, comprising a resin and a linker compound, wherein the support is a compound of formula II:

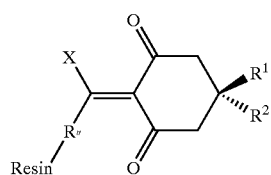

in which

X is OH;

$R^1$ is hydrogen or $C_{1-4}$ alkyl, $R^2$ is hydrogen or $C_{1-4}$ alkyl; and

R" is an alkyl, substituted alkyl, aryl, substituted aryl, cycloalkyl, or substituted cycloalkyl spacer group that is directly coupled to the resin support or that is coupled to the resin via a functionality that is stable to conditions of oligosaccharide synthesis and cleavage.

13. The support of claim 12, in which $R^1$ and $R^2$ are both methyl.

14. The support of claim 12, in which the functionality is —CONH—, —S—, —S—, —COO—, —CH=N—, —NHCONH—, NHCSNH, or —NHNH— grouping.

15. The support of claim 12, in which the functionality is —COO— or —CONH—.

16. The support of claim 12, in which the linker compound is 6-hydroxy-6-(4,4-dimethyl-2,6-dixocyclohexylidene)-hexanoic acid or an ester thereof.

17. The support of claim 16, in which the linker compound is a benzyl, methyl or t-butyl ester of the compound 6-hydroxy-6-(4,4-dimethyl-2,6-dixocyclohexylidene)-hexanoic acid.

18. A kit for solid phase synthesis or combinatorial synthesis of oligosaccharides, the kit comprising a resin-linker support of claim and one or more protecting agents, deprotecting agents or solvents suitable for solid phase or combinatorial synthesis of oligosaccharides.

19. A method of synthesis of a resin-linker support of claim 12, in which said method comprises reaction of a resin with an activated dicarboxylic acid or anhydride followed by reaction with a 1,3-dioxocycloalkane compound.

20. The method of claim 19, in which said 1,3-dioxocycloalkane compound is 5,5-dimethyl-1,3-cyclohexanedione.

21. The method of claim 19, in which said dicarboxylic acid is adipic acid or glutaric acid or an anhydride thereof.

22. A method of solid-phase synthesis of oligosaccharides, comprising sequentially linking mono- or oligosaccharide groups to the resin-linker-saccharide support of claim 12.

* * * * *

UNITED STATES PATENT AND TRADEMARK OFFICE
CERTIFICATE OF CORRECTION

PATENT NO. : 6,573,337 B1  
DATED : June 3, 2003  
INVENTOR(S) : Toth et al.

It is certified that error appears in the above-identified patent and that said Letters Patent is hereby corrected as shown below:

Column 23,  
Lines 18-26, delete "

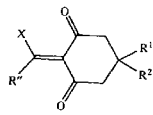

" and insert --

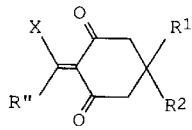

III

-- therefor.

Column 24,  
Lines 5-13, delete "

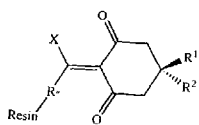

" and insert --

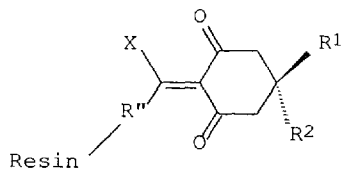

II therefor.

UNITED STATES PATENT AND TRADEMARK OFFICE
CERTIFICATE OF CORRECTION

PATENT NO. : 6,573,337 B1
DATED : June 3, 2003
INVENTOR(S) : Toth et al.

It is certified that error appears in the above-identified patent and that said Letters Patent is hereby corrected as shown below:

<u>Column 24 cont'd,</u>
Line 28, delete "—S—" and insert -- —O— -- therefor.
Line 42, delete "claim" and insert -- claim 12 -- therefor.

Signed and Sealed this

Seventeenth Day of February, 2004

JON W. DUDAS
*Acting Director of the United States Patent and Trademark Office*